(12) United States Patent
Garti et al.

(10) Patent No.: US 11,666,618 B2
(45) Date of Patent: Jun. 6, 2023

(54) METHOD FOR SELECTIVE EXTRACTION OF CANNABINOIDS FROM A PLANT SOURCE

(71) Applicant: Yissum Research Development Company of the Hebrew University of Jerusalem Ltd., Jerusalem (IL)

(72) Inventors: Nissim Garti, Ramat HaSharon (IL); Sharon Garti Levi, Modi'in (IL); Rotem Edri, Eilat (IL)

(73) Assignee: YISSUN RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 16/338,259

(22) PCT Filed: Sep. 28, 2017

(86) PCT No.: PCT/IL2017/051099
§ 371 (c)(1),
(2) Date: Mar. 29, 2019

(87) PCT Pub. No.: WO2018/061009
PCT Pub. Date: Apr. 5, 2018

(65) Prior Publication Data
US 2019/0231833 A1    Aug. 1, 2019

(30) Foreign Application Priority Data
Sep. 29, 2016 (IL) .......................... 248150

(51) Int. Cl.
| | | |
|---|---|---|
| A61K 36/185 | (2006.01) |
| A61K 9/00 | (2006.01) |
| A61K 9/70 | (2006.01) |
| A61K 9/48 | (2006.01) |
| A61K 9/08 | (2006.01) |
| A61K 9/107 | (2006.01) |
| A61K 9/06 | (2006.01) |
| A61K 47/44 | (2017.01) |
| A61K 47/14 | (2017.01) |
| A61K 47/24 | (2006.01) |
| A61K 47/10 | (2017.01) |
| B01D 11/02 | (2006.01) |
| A61K 47/26 | (2006.01) |
| A61K 31/352 | (2006.01) |

(52) U.S. Cl.
CPC .......... *A61K 36/185* (2013.01); *A61K 9/0014* (2013.01); *A61K 9/0019* (2013.01); *A61K 9/0043* (2013.01); *A61K 9/0048* (2013.01); *A61K 9/0053* (2013.01); *A61K 9/0073* (2013.01); *A61K 9/06* (2013.01); *A61K 9/08* (2013.01); *A61K 9/1075* (2013.01); *A61K 9/48* (2013.01); *A61K 9/7015* (2013.01); *A61K 9/7023* (2013.01); *A61K 31/352* (2013.01); *A61K 47/10* (2013.01); *A61K 47/14* (2013.01); *A61K 47/24* (2013.01); *A61K 47/26* (2013.01); *A61K 47/44* (2013.01); *B01D 11/0288* (2013.01); *A61K 2236/00* (2013.01); *A61K 2236/30* (2013.01)

(58) Field of Classification Search
CPC ....................................................... A61K 36/00
USPC ............................................................ 424/725
See application file for complete search history.

(56) References Cited

U.S. PATENT DOCUMENTS

| | | |
|---|---|---|
| 2006/0217445 A1 | 9/2006 | Chew et al. |
| 2007/0104741 A1 | 5/2007 | Murty et al. |
| 2008/0279940 A1 | 11/2008 | Rigassi et al. |
| 2008/0300386 A1 | 12/2008 | Lazarev et al. |
| 2012/0004319 A1 | 1/2012 | Shimizu et al. |
| 2013/0089600 A1 | 4/2013 | Winnicki |
| 2016/0081927 A1 | 3/2016 | Bromley |
| 2017/0042808 A1 | 2/2017 | Hirai et al. |
| 2017/0181940 A1 | 6/2017 | Richard |
| 2017/0232210 A1 | 8/2017 | Boeckl et al. |
| 2018/0042845 A1* | 2/2018 | Sinai .................. A61K 47/10 |
| 2019/0231833 A1 | 8/2019 | Garti et al. |

FOREIGN PATENT DOCUMENTS

| | | |
|---|---|---|
| CN | 1547479 A | 11/2004 |
| CN | 102145084 A | 8/2011 |
| CN | 103110582 A | 5/2013 |
| CN | 103690580 A | 4/2014 |
| CN | 104619318 A | 5/2015 |
| CN | 105535111 A | 5/2016 |
| CN | 105997985 A | 10/2016 |
| EP | 1 155 698 A1 | 11/2001 |
| EP | 2 223 913 A1 | 9/2010 |
| IL | 165 528 A | 11/2010 |
| KR | 10-2007-0117578 A | 12/2007 |
| WO | 03/105607 A1 | 12/2003 |
| WO | 2004/056322 A2 | 7/2004 |

(Continued)

OTHER PUBLICATIONS

Fischer et al., Journal of Colloid and Interface science, 453, 2015, 186-193.*

Chodchanok Attaphong, et al., "Phase Behaviors of Vegetable Oil-Based Microemulsion Fuels: The Effects of Temperatures, Surfactants, Oils, and Water in Ethanol", ACS Publications, published Oct. 7, 2013, Downloaded via Tel Aviv Univ on Sep. 19, 2022 at 12:39:48 (UTC), pp. 6773-6780.

(Continued)

*Primary Examiner* — Michael V Meller
(74) *Attorney, Agent, or Firm* — Xsensus LLP

(57) ABSTRACT

Provided are methods for selective extraction of cannabinoids, for example cannabidiol (CBD), from a plant source, by using tailored extraction media.

7 Claims, 17 Drawing Sheets

(56) References Cited

FOREIGN PATENT DOCUMENTS

| | | | |
|---|---|---|---|
| WO | 2006/094829 | A1 | 9/2006 |
| WO | 2008/058366 | A1 | 5/2008 |
| WO | 2013/044579 | A1 | 4/2013 |
| WO | 2013/108254 | A1 | 7/2013 |
| WO | 2014/031504 | A1 | 2/2014 |
| WO | 2015/011724 | A2 | 1/2015 |
| WO | 2016/004410 | A1 | 1/2016 |
| WO | 2016/022936 | A1 | 2/2016 |
| WO | 2016/064987 | A1 | 4/2016 |
| WO | 2018/061007 | A1 | 4/2018 |
| WO | 2018/061011 | A1 | 4/2018 |

OTHER PUBLICATIONS

Linh D. Do, et al., "Environmentally Friendly Vegetable Oil Microemulsions Using Extended Surfactants and Linkers", Springer AOCS, Article in Journal of Surfactants and Detergents • May 2008, 10 pp.
Amsalem et al., "Phospholipids-embedded fully dilutable liquid nanostructures. Part 2: The role of sodium diclofenac", Colloids and Surfaces B: Bioterfaces, (2010), vol. 81, No. 2, pp. 422-429.
Database Medline, Lu et al., Apr. 2009. "Study on extraction of quercetin in guava leaf by microemulsion" XP002776489.
Database Medline, Yue et al., May 2014. "Study on extracting and separating curcuminoids from Curcuma longa rhizome using ultrasound strengthen by microemulsion" XP002776488.
Deutch-Kolevzon et al., "Synergistic cosolubilization of omega-3 fatty acid esters and CoQ10 in dilutable microemulsions", Chemistry and Physics of Lipids, (2011), vol. 164, pp. 654-663.
Fisher et al., "Solubilization of simvastatin and phytosterols in a dilutable microemulsion system", Colloids and Sufaces B.: Biointerfaces, (2013), vol. 107, pp. 35-42.
Garti et al., "Nano-sized self assemblies of nonionic surfactants as solubilization reservoirs and microreactors for food systems", Soft Matter Journal, (2005), vol. 1, pp. 206-218.
Lee et al., "Comparison of the Antioxidant and Transmembrane Permeative Activities of the Different Polygonum cuspidatum Extracts in Phospholipid-Based Microemulsions", Journal of Agricultural and Food Chemistry, (2011), vol. 59, pp. 9135-9141.
Liu et al., "A new biocompatible microemulsion increases extraction yield and bioavailability of Andrographis paniculata", Chinese Journal of Natural Medicines, (2016), vol. 14, No. 9, pp. 683-691.
Spernath et al., "Microemulsions as carriers for drugs and nutraceuticals", Adv. in Colloid and Interface Science Journal, (2006), vol. 128, pp. 47-64.
Spernath et al., "Fully dilutable microemulsions embedded with phospholipids and stabilized by short-chain organic acids and polyols", Journal of Colloid and Interface Science, (2006), vol. 299, pp. 900-909.
Spernath et al., "Phase Transition Induced by Water Dilution in Phospholipid U-Tyoe Food-Grade Microemulsions Studied by DSC", Journal of Thermal Analysis and Calorimetry, (2006), vol. 83, Issue 2, pp. 297-308.
Spernath et al., "Phosphatidylcholine embedded microemulsions: Physical properties and improved Caco-2 cell permeability", Journal of Controlled Release, (2007), vol. 119, pp. 279-290.
Vandamme, "Microemulsions as ocular drug delivery systems: recent developments and future challenges", Progress in Retinal and Eye Research, (2002), vol. 21, No. 1, pp. 15-34.
Patil et al., "Phytosomes: Increasing Biovailability of Phytoconstituents", Int J of Universal Pharmacy and Bio Sciences, 2016, vol. 5, No. 4, pp. 81-94.
Hua et al., "Experiment of Extracting Salviae Miltiorthizae on using OW Microemulsion", China Journal of Chinese Materia Medica, vol. 33, Issue 22, four pages.

* cited by examiner

METHOD FOR SELECTIVE EXTRACTION OF CANNABINOIDS FROM A PLANT SOURCE

TECHNOLOGICAL FIELD

The present disclosure provides methods for selective extraction of cannabinoids, for example cannabidiol (CBD), from a plant source, by using tailored extraction media.

BACKGROUND ART

References considered to be relevant as background to the presently disclosed subject matter are listed below:
[1] WO 2008/058366
[2] A. Spernath, A. Aserin, *Advances in Colloid and Interface Science* 2006, 128
[3] A. Spernath, A. Aserin, N. Garti, *Journal of Colloid and Interface Science* 2006, 299, 900-909
[4] A. Spernath, A. Aserin, N. Garti, *Journal of Thermal Analysis and Calorimetry* 2006, 83
[5] N. Garti, A. Spernath, A. Aserin, R. Lutz, *Soft Matter* 2005, 1
[6] A. Spernath, A. Aserin, L. Ziserman, D. Danino, N. Garti, *Journal of Controlled Release* 2007, 119
[7] S. Fisher, E. J. Wachtel, A. Aserin, N. Garti, *Colloids and Surfaces B: Biointerfaces* 2013, 107, 35-42
[8] R. Deutch-Kolvzon, A. Aserin and N. Garti, *Chemistry and Physics of Lipids* 2011, 164(7), 654
[9] O. Amsalem, A. Aserin, N. Garti, Colloids and Surfaces, B: Biointerfaces 2010, 81(2), 422-429.

Acknowledgement of the above references herein is not to be inferred as meaning that these are in any way relevant to the patentability of the presently disclosed subject matter.

BACKGROUND

Cannabinoids have been used for many years, inter alia in alleviating pain and inflammatory-related syndromes, spasms, asthma, sleep disorders, depression, loss of appetite and other medical conditions. The cannabinoids are a family of active compounds found mainly in the resin-producing pistillate inflorescences of cannabis plants. Although a variety of cannabinoid compounds have been identified in literature thus far, two compounds in particular have been the main focus of interest for medicinal uses: tetrahydrocannabinol (THC) and cannabidiol (CBD).

While THC is a psychoactive compound with adverse long-lasting effects on the user, CBD is not regarded as a psychotropic agent and is considered safe for consumption in various routes of administration. Both compounds are typically found as a mixture, at various concentration ranges, in the plant source. For formulating into pharmaceutical compositions, the cannabinoids are often extracted from the plant source by various methods.

One of the methods commonly used is extraction by carrier oils, in which the carrier oil is used as a solvent for the extraction of the cannabinoid species from the plant source. Since the oil-filled trichomes of the inflorescences are fat-soluble, natural plant oils are an effective way to extract the mixture of cannabinoid species from the cannabinoid-laden resin and other parts of plant.

Another method often used is extraction by organic solvents capable of dissolving cannabinoids. Such extraction requires tailoring of the solvent for effective extraction, and often results in low yields of extraction. Further, it is difficult to remove traces of the solvent from the end product, reducing the degree of purity and the safety of the resulting extract. Most of these extractions are found to be insufficient and often leave undesired traces of the solvent (especially when petroleum ethers are used).

A further method which is used for obtaining extraction of various compounds from various plant sources is super-critical $CO_2$ extraction. In the $CO_2$ extraction process, $CO_2$ at super-critical conditions (i.e. high temperature and pressure) is used for extraction of the cannabinoid species. Although relatively effective for extracting a variety of compounds from the plant source, this technique is often more complicated, time consuming and very expensive compared to liquid extraction. In addition, this technique is far from being selective for specific cannaboids, and may concomitantly extract also various essential oils.

Although various methods exist for extraction of cannabinoids, these all have the common disadvantage of low extraction yield and low (or no) selectivity. Namely, the extraction methods known to date extract various species of cannabinoids from the plant source, often resulting in a mixture of various concentrations and ratios of CBD and THC, hindering subsequent formulation and use of CBD in pharmaceutical compositions.

Thus, there exists a need for a highly selective extraction process for obtaining high loads of specific cannabinoids, such as CBD, from a mixture of cannabinoids-containing plant source.

GENERAL DESCRIPTION

High selectivity to specific cannabinoids, such as CBD, is provided in the present disclosure by the use of a unique one-pot extraction process utilizing a tailored extraction medium. As further detailed herein, the process of this disclosure provides a product which is highly-loaded with a desired cannabinoid (e.g. CBD) with lower levels of other cannabinoids, in particular THC. In addition, the present disclosure provides extraction medium formulations enabling the selective extraction of desired cannabinoids, as well as various pharmaceutical compositions and administration forms comprising it.

In one of its aspects, the present disclosure provides a process for extraction of cannabinoids, for example cannabidiol (CBD), from a plant source, the process comprising:
(a) obtaining a first mixture comprising a first quantity of a cannabinoid-containing (e.g. CBD-containing) plant source and a first quantity of an extraction medium, the extraction medium comprising at least one oil, at least one hydrophilic surfactant and at least one co-surfactant, and optionally comprising at least one co-solvent;
(b) homogenizing the first mixture; and,
(c) separating the homogenized mixture into a biomass slurry and a cannabinoid (e.g. CBD)-loaded medium.

The process of the invention utilized microemulsions as extraction medium for the cannabinoids, and may be tailored for selective extraction of a desired cannabinoid from the plant source. The extraction medium may be tailored, for example, to extract mainly CBD, mainly THC, or other cannabinoids present in the plant source as will be further explained below. Microemulsions (MEs) are well-known vehicles for delivery of drugs because of their spontaneous formation, high solubilization capacity, low viscosity, transparency, Newtonian behavior and physical thermodynamic stability [1]. A specific type of microemulsion are nano-sized self-assembled liquids, which have been previously studied and their ability to solubilize non-soluble drugs and nutraceuticals has been demonstrated [2-7]. The extraction media are self-assembled microemulsions systems of nanodroplets, comprising surfactants and oil. The extraction medium of the present disclosure, as will be explained further herein, comprise at least one oil, at least one hydrophilic surfactant and at least one solvent, and may further comprise, additional components such as co-surfactants, co-solvents and phospholipids. In the present disclosure, the term microemulsion(s) will refer to extraction medium, unless otherwise defined. The terms "microemulsion" and "extraction medium" will be used interchangeably.

The extraction medium may be in the form of water-free concentrates that can be fully and progressively diluted with aqueous phase to form swollen micellar systems or oil-in-water microemulsions. The diluted microemulsions (diluted medium) are nano-sized uniform (mono-dispersed) structures, exhibiting zero interfacial tension between the oil phase and the aqueous phase, and behaving like Newtonian fluids. The medium is self-assembled upon mixing the surfactants and the oil to form water-free reverse micelles. Upon dilution with water or aqueous solutions, water-swollen micelles or water-in-oil nanodroplets are formed, being able to invert into bicontinuous mesophases in the presence of an aqueous phase, e.g. water. Upon further dilution, they undergo (umbrella type) inversion into oil-in-water droplets.

Without wishing to be bound by theory, these systems are constituted by oil-solvated clusters or short domains of surfactants, however differ from the classical reverse micelles. When mixed with small amounts of aqueous media hydrated and solvated surfactants are formed, and upon further dilution with aqueous phase they are easily transform into oil-in-water (O/W) nanodroplets entrapping into their core the extracted cannabinoid molecules. The transformation to O/W microemulsions is spontaneous, i.e. without the need to employ shearing, mechanical forces or excessive heating conditions. The CBD and/or other extracted cannabinoids are entrapped in the core of the reverse micelles and remains at the interface between the oil phase and the aqueous phase upon dilution in the bicontinuous region; thereafter the cannabinoid molecules are located in the core of the droplets once the O/W microemulsion is formed. The interactions (physical complexation) between the CBD and the surfactants (as well as the co-surfactants, when used) allow maintaining the extracted cannabinoid within the oil core throughout the structural transformations of the reverse micelles into a bicontinuous region and finally to the O/W microemulsion, thus stabilizing the formulation and preventing undesired release of the cannabinoid from the oil core prior to its administration (i.e. during storage).

These extraction media are thermodynamically stable, with nano-sized droplets, which may be safely stored for prolonged periods of time, without creaming, aggregation, coalescence or phase separation. The cannabinoid-loaded medium prepared by the process of this disclosure is also characterized by a substantially uniform and stable droplets size, typically in the nanometric scale and having a narrow size distribution. The stability of the droplet size is of importance as changes in the droplet size may impair the release of the entrapped (solubilized) extracted molecules within the droplets once the microemulsion is administered. Further, the loaded media, when not in diluted form, are devoid of water, and as such do not support (or minimize) microbial growth. Further, due to their high stability and small droplet size, these systems may be sterilized without the risk of self-contamination in various ways, such as heat sterilization, filtration through a 0.22 um filter, UV and other methods know to the art, and without damaging the medium's beneficial structure.

In the present disclosure, the systems are designed (i.e. by selecting the composition of the surfactants, oil and co-surfactants) to extract specific desired cannabinoid (such as CBD, CBDA, THC and others) from a plant source, such that the cannabinoid-loaded medium is substantially water-free (i.e. containing up to 10 wt % water), and can be easily diluted or further formulated "on demand" and as per application or route of administration with any type of aqueous solution (buffer, water for injection, saline, isotonic mixtures and others).

Cannabinoids are a group of psychoactive and non-psychoactive compounds which have an activity on cannabinoid receptors in cells to repress neurotransmitter release in the brain. The term is meant to encompass cannabinoids which are obtained from natural sources. The cannabinoid may be selected from one or more of cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CDB), cannabidiol monomethylether (CBDM), cannabidiol-$C_4$ (CBD-$C_4$), cannabidivarinic acid (CBDVA), cannabidiorcol (CBD-$C_1$), delta-9-tetrahydrocannabinolic acid A (THCA-A), delta-9-tetrahydrocannabinolic acid B (THCA-B), delta-9-tetrahydrocannabinol (THC), delta-9-tetrahydrocannabinolic acid-$C_4$ (THCA-$C_4$), delta-9-tetrahydrocannabinol-$C_4$ (THCA-$C_4$), delta-9-tetrahydrocannabivarinic acid (THCVA), delta-9-tetrahydrocannabivarin (THCV), delta-9-tetrahydrocannabiorcolic acid (THCA-$C_1$), delta-9-tetrahydrocannabiorcol (THC-$C_1$), delta-7-cis-iso-tetrahydrocannabivarin, delta-8-tetrahydrocannabinolic acid A ($\Delta^8$-THCA), delta-8-tetrahydrocannabinol ($\Delta^8$-THC), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-$C_4$ (CBN-$C_4$), cannabivarin (CBV), cannabinol-$C_2$ (CBN-$C_2$), cannabiorcol (CBN-$C_1$), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (cis-THC), 3,4,5,6-tetrahtdro-7-hydroxy-α-α-2-trimethyl-9-n-propyl-2,6-methano-2H-1-benzoxocin-5-methanol (OH-iso-HHCV), cannabiripsol (CBR), trihydroxy-delta-9-tetrahydroxycannabinol (triOH-THC), and any other cannabinoid.

In some embodiment, the desired cannabinoid is CBD or CBDA.

In some embodiments, CBD is extracted selectively from a plant source that includes a mixture of various cannabinoids.

Cannabidiol (CBD) refers herein to a class of non-psychoactive cannabinoids with little affinity to CB1 and CB2 receptors, having a formula $C_{21}H_{30}O_2$ and a general structure of Formula I.

Formula I

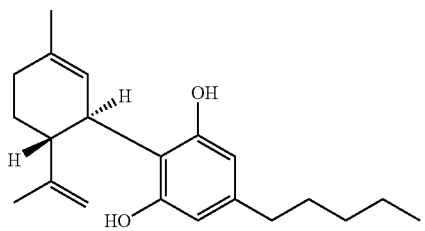

Tetrahydrocannabinol (THC) refers herein to a class of psychoactive cannabinoids characterized by high affinity to CB1 and CB2 receptors, having a molecular formula $C_{21}H_{30}O_2$ and a general structure of Formula II:

Formula II

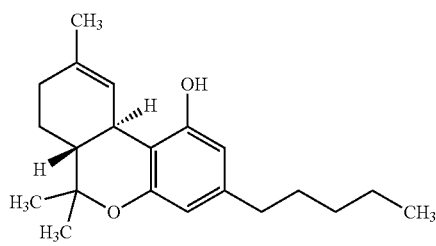

In the context of the present disclosure, the terms CBD and THC are meant to encompass also isomers, derivatives, or precursors of these molecules, such as (−)-trans-Δ9-tetrahydrocannabinol (Δ9-THC), Δ8-THC, and Δ9-CBD, and to CBD and THC derived from their respective 2-carboxylic acids (2-COOH), CBDA and THCA, respectively.

As noted above, the process of the present disclosure permits selective and quantitative extraction of cannabinoids, such as CBD from a plant source that, in some embodiments, comprises mainly CBD and THC. The term selectively or selective extraction means to denote that the process permits obtaining an extraction product which is highly enriched in the desired cannabinoid, with little or no presence of an undesired cannabinoid.

In some embodiments, the process and extraction medium are tailored to selectively extract CBD, such that the CBD-loaded medium contains no more than 3 wt % of THC. In other embodiments, the process and extraction medium are tailored to selectively extract CBD, such that the CBD-loaded medium contains no more than 1 wt % of THC. Namely, products of the process of this disclosure are, by some embodiments, spent biomass which is enriched with THC (i.e. as a result from the extraction) and the CBD-loaded medium that comprises at most 3 wt %, at most 2.5 wt %, at most 2 wt %, at most 1.5 wt %, at most 1 wt % THC, at most 0.8 wt % THC, at most 0.6 wt % THC, at most 0.5 wt % THC, or even at most 0.1 wt % THC. It is of note that the wt % THC refers to weight percentage of THC out of the extracted cannabinoid (not from the THC content in the plant source).

According to other embodiments, the selectivity of the medium enables obtaining a CBD-loaded medium in which the ratio between CBD and THC is between about 10:1 and about 40:1.

In some embodiments, the cannabinoid-loaded medium comprises between about 0.1 and 12 wt % of CBD. In other embodiments, the cannabinoid-loaded medium may comprise between about 0.1 and 11 wt % of CBD, between about 0.1 and 10 wt % of CBD, between 0.1 and 9 wt % CBD, or between about 0.1 and 8 wt % of CBD. In some other embodiments, the cannabinoid-loaded medium may comprise between about 0.5 and 12 wt % of CBD, between about 1 and 12 wt % of CBD, between 1.5 and 12 wt % CBD, or between about 2 and 12 wt % of CBD. In additional embodiments, the cannabinoid-loaded medium may comprise between about 0.5 and 11 wt % of CBD, between about 1 and 10 wt % of CBD, between 1.5 and 9 wt % CBD, or between about 2 and 8 wt % of CBD.

When referring to the plant source, it is to be understood that the raw-material from which the desired cannabinoid are extracted is a plant from the genus *Cannabis*. In some embodiments, the plant source is selected from *Cannabis sativa, Cannabis indica, Cannabis ruderalis*, and any mixture thereof. The plant source may be any naturally-occurring strain, any horticultural variant, cultivated or engineered strain categorized in the *Cannabis* genus.

The process of this disclosure may be carried out utilizing any part of the plant source that may contain the desired cannabinoid; i.e. in some embodiments, the plant source is selected from Cannabis flowers, inflorescences, buds, fruit, pericarp, seeds, leaves, stems, stalks, roots, and any mixture thereof.

The plant source may be provided in any desired form, for example, as a powder, granules, pellets, tablets, flakes, shreddings, or a plant part (e.g. intact leaves, seeds, intact inflorescence, etc.). The plant source may be provided fresh, semi-desiccated or desiccated, frozen, freeze-dried, etc.

As noted above, the extraction medium used for extraction in the process of this disclosure comprises at least one oil, at least one hydrophilic surfactant, and at least one co-surfactant, optionally comprising at least one solvent and/or co-solvent.

In the context of the present disclosure, the term oil refers to natural or synthetic oil in which the desired cannabinoid is solubilized. The oils used in the extraction media of this disclosure may be approved for administration to a subject. In some embodiments, the oil may be selected from including essential oils (such as R-limonene, D-limonene, terpenes or terpene-less), mineral oil, paraffinic oils, phospholipids, polar lipids (squalenes, spingomelines), waxes, vegetable oils, triglycerides, glycerides, fatty acids and esters of fatty acids, liquid hydrocarbons and others, and any mixture thereof.

According to some embodiments, the oil may be selected from medium-chain triglycerides (MCT), olive oil, soybean oil, canola oil, cotton oil, palmolein, sunflower oil, corn oil, isopropyl myristate, oleyl lactate, coco caprylocaprate, hexyl laurate, oleyl amine, oleic acid, oleyl alcohol, linoleic acid, linoleyl alcohol, ethyl oleate, hexane, heptanes, nonane, decane, dodecane, D-limonene, triacetin, neem oil, lavender oil, peppermint oil, anise oil, menthol, capsaicin, grape seed oil, pomegranate oil, avocado oil, sesame oil, fish oil, omega oils and omega fatty acids, and similar essential oils and mixtures thereof.

According to other embodiments, the oil is selected from at least one medium-chain triglyceride (MCT), castor oil, R-(+)-Limonene, glycerol, oleic acid, triacetin, isopropyl myristate, ethyl laurate, olive oil, benzyl alcohol, laurylacetate, lauryl lactate, oleyl lactate, cetyl alcohol, ethyl hexyl laurate, ethyl hexyl oleate, and others.

The oil may be present in the extraction medium, according to some embodiments, at an amount of between about 0.5 and 20 wt %.

The extraction medium comprises at least one hydrophilic surfactant. The term hydrophilic surfactant refers to ionic or non-ionic surfactants having a hydrophilic nature, i.e. a surfactant having an affinity for water. Exemplary surfactants are polyoxyethylene sorbitan monolaurate, polyoxyethylene sorbitan monopalmitate, polyoxyethylene sorbitan monooleate, and polyoxyeyhylene esters of saturated and unsaturated castor oil, palmitostearate, ethoxylated monoglycerol esters, ethoxylated fatty acids, ethoxylated fatty acids of short and medium and long chain fatty acids and others.

In some embodiments, the at least one hydrophilic surfactant is selected from Solutol HS15 (polyethylene glycol (15)-hydroxystearate), polyoxyethylenes, ethoxylated (20EO) sorbitan mono laurate (T20), ethoxylated (20EO) sorbitan monostearate/palmitate (T60), ethoxylated (20EO) sorbitan mono oleate/linoleate (T80), ethoxylated (20EO) sorbitan trioleate (T85), castor oil ethoxylated (20EO to 40EO); hydrogenated castor oil ethoxylated (20 to 40EO), ethoxylated (5-40 EO) monoglyceride stearate/plamitate, polyoxyl 35 and 40 EOs castor oil. According to other embodiments, the hydrophilic surfactant may be selected from glycerol, polyoxyl 35 castor oil, polysorbate 40 (Tween 40), polysorbate 60 (Tween 60), polysorbate 80 (Tween 80), Mirj S40, Oleoyl macrogolglycerides, Polyglyceryl-3 dioleate, ethoxyllated hydroxyl stearic acid (Solutol HS15), sugar esters (sucrose mono oleate, sucrose mono stearate), polyglycerol esters (10 glycerol mono oleate, 6 glycerol monolaurate, or mono oleate); and soaps such as sodium-, potassium-, ammonium-, ethanol amine- of a short and medium chain saturated and unsaturated fatty acids (e.g. sodium laurate, sodium oleate, sodium linoleate, sodium linoleneate and others), and any combination thereof. The extraction medium may comprise, by some embodiments, between about 30 and 85 wt % of said hydrophilic surfactant.

The term co-surfactant should be understood to encompass any agent, different from the hydrophilic surfactant, which is capable (together with the hydrophilic surfactant) of lowering the interfacial tension between the oil phase and an aqueous phase to almost zero (or zero) allowing for the formation of a homogeneous mixture, as well as geometrical and physical integration of the extracted cannabinoid into the interface or the oily core of the nanostructures once the medium is mixed with an aqueous liquid. According to some embodiments, the co-surfactant is selected from polyols, diglycerides, polyoxyethylenes, and others.

The co-surfactant may be at least one polyol, i.e. an alcohol containing at least 2 hydroxyl groups, for example ethylene glycol, glycerol, polyethylene glycol, polypropylene glycol, sorbitol, mannitol, lactitol, xylitol and others.

In some embodiments, the co-surfactant may be selected from glycerol, polypropylene glycol, polyethylene glycol, sorbitol, xylitol, PEG 200, PEG 400 and PEG 600. In some embodiments, the co-surfactant is present in the extraction medium at an amount of between about 1 and 50 wt %.

In some embodiments, the extraction medium may further comprise at least one solvent. The term solvent refers to an organic compound, different from the oil, which is miscible in the oil and together therewith forms a homogenous oily phase that dissolves and stabilizes CBD. The solvent may, according to some embodiments, be selected liquid hydrocarbons, alcohols, and others. According to some embodiments, the solvent may be selected from ethanol, propanol, isopropanol, acetic acid, lactic acid, fumaric acid, malic acid, tartaric acid, succinic acids and others. In some embodiments, the solvent may be present in the extraction medium at an amount of between about 0.1 and 25 wt %.

The co-solvent may be a polyol, such as propylene glycol, glycerol, xylitol or short chain alcohols such as ethanol, propanol, iso-propanol and others.

In some embodiments, the extraction medium further comprises at least one phospholipid. Phospholipids such as soy lecithins, rapeseed lecithins, corn or sunflower lecithins, egg lecithins, hydroxylated phospholipids, lyso phospholipids, phosphased phospholipids, hydrogenated phospholipids, Epicorn 200, Phosal 50 PG, dioleyl phospatidylcholine (DOPC), oleyl palmytoyl phosphatidylcholine (POPC), and the corresponding serines, ethanol amines, glycerol, and others may be used. According to such embodiments, the extraction medium may comprise between about 1 and 10 wt % of phospholipids.

As a man of the art may appreciate, the ratio between the medium's components may be tailored to endow certain characteristics to the extraction medium (such as, desired cannabinoid (e.g. CBD) loading, droplet size, viscosity, electrical charge, etc.).

In some embodiments, the extraction medium comprises (i) at least one oil selected from medium chain triglyceride (MCT), R-(+)-limonene, triacetin, and oleic acid, (ii) at least one hydrophilic surfactant selected from polysorbate 80 (Tween 80), polyoxyl 35 castor oil (cremophor castor oil), palmitostearate (labrasol), sucrose mono-/di-laurate, and glycerol, and (iii) polypropylene glycol (PG) as co-surfactant, and optionally at least one phospholipid and/or at least one solvent selected from ethanol and isopropyl alcohol.

In other embodiments, the extraction medium is selected from the following extraction media formulations:
  medium chain triglyceride (MCT), polysorbate 80 (Tween 80), polyoxyl 35 castor oil (cremophor castor oil), polypropylene glycol (PG), and at least one phospholipid; or
  R-(+)-limonene, polysorbate 80 (Tween 80), polypropylene glycol (PG), and at least one solvent selected from ethanol and isopropyl alcohol; or
  triacetin, polyoxyl 35 castor oil (cremophor castor oil), palmitostearate (labrasol), polypropylene glycol (PG), at least one phospholipid, and at least one solvent selected from ethanol and isopropyl alcohol; or
  medium chain triglyceride (MCT), sucrose mono-/di-laurate, polypropylene glycol (PG), at least one phospholipid, and at least one solvent selected from ethanol and isopropyl alcohol; or
  medium chain triglyceride (MCT), oleic acid, polysorbate 80 (Tween 80), polyoxyl 35 castor oil (cremophor castor oil), glycerol, polypropylene glycol (PG), at least one phospholipid, and at least one solvent selected from ethanol and isopropyl alcohol.

The plant source of the present disclosure is extracted by utilizing the extraction medium. The term extraction or any lingual variation thereof, is meant to denote the transfer of desired cannabinoids from the plant source to a solubilizing oily phase of the extraction medium. The process of the present disclosure comprises obtaining a first mixture of the plant source and the extraction medium, for example by mixing. Mixing may be carried out by any suitable known method that does not involve sheer-mixing, for example, manual mixing, magnetically stirring, mixing by pedals, and others.

In some embodiments, the weight ratio (wt/wt) of the first quantity of plant source to the first quantity of extraction medium is between 1:5 and 1:100. In other embodiments, the weight ratio (wt/wt) of the first quantity of plant source to the first quantity of extraction medium may be between 1:7 and 1:90, 1:10 and 1:80, 1:12 and 1:70, or even between 1:15 and 1:60.

In the next stage, the first mixture is homogenized. Homogenization, or any lingual variation thereof, refers to the process of applying sheer forces onto mixtures to break down both the plant source (i.e. reduce the plant source in size) and the extraction medium and blend them to form intimate contact that permits the extraction of the desired cannabinoid from the plant source. Homogenization may be carried out by any suitable means, including, but not limited to homogenizers and high speed mechanical stirring. It is of note that as the media used in the process of this disclosure have a nanometric size structure, and therefore the homogenization process has little impact with respect to the micelles size and/or structure of the extraction medium.

In some embodiments, the homogenization (i.e. of step (b)) may be carried out for a period of time of between about 1 minute and about 120 minutes. In other embodiments, the homogenization is carried out for a period of between about 1 minute to 60 minutes, between about 1 minute and 45 minutes, between about 1 minute and 30 minutes, or even between about 1 minute and 20 minutes. In some other embodiments, the homogenization may be carried our between about 5 minutes and about 120 minutes, between about 10 minutes and about 120 minutes, between about 15 minutes and about 120 minutes, or even between about 20 minutes and about 120 minutes.

According to some embodiments, homogenization may be carried out at a pressure of between about 500 and 6,000 psi.

In some embodiments, the homogenization may be carried out at a temperature of between about 5 and about 70° C. In other embodiments, the homogenization may be carried out at a temperature of between about 10 and about 70° C., between about 15 and about 70° C., between about 20 and about 70° C., between about 25 and about 70° C. or between about 30 and about 70° C. In some other embodiments, the homogenization may be carried out at a temperature of between about 10 and about 65° C., between about 10 and about 60° C., between about 10 and about 55° C., between about 10 and about 50° C., between about 10 and about 45° C., or even between about 10 and about 40° C. In further embodiments, the homogenization may be carried out at a temperature of between about 5 and about 60° C., between about 20 and about 50° C., or between about 25 and about 45° C.

Homogenization may be carried out by using any suitable type of homogenizer, for example a Silverstone homogenizer, an ultra-torque homogenizer, colloid mill, sonication, ball milling, microfluidizer and other homogenization, emulsification or dispersion methods that employ high shear and high mechanical forces or pressure.

Once the mixture has been homogenized, the mixture is separated into a biomass slurry that includes the spent plant source, and a cannabinoid-loaded medium (e.g. a CBD-loaded medium). Separating may be carried by any suitable method, for example by filtering through a filter or by centrifugation, decantation or aspiration of extract phase. In some embodiments, separating the mixture is carried out by centrifugation, which may or may not be followed by filtration.

It is of note that often at least a portion of the cannabinoid may be found in the plant in its carboxylated form. For example, the majority of CBD is found in the plant as CBDA. Thus, it is often desired to transform the carboxylated form into the non-carboxylated form; for example, transforming CBDA into CBD, that is known to have pharmacological activity. In the presently disclosed process, such transformation may be afforded by heating the plant source prior to extraction, thereby decarboxylating the cannabinoid (e.g. CBDA into CBD). Thus, in some embodiments, the process may further comprise, prior to step (a), heating of the plant source.

In some other cases the heating can be done at a later stage, in which heating is carried out on the CBDA-loaded medium (i.e. after the extraction).

According to some embodiments, the plant source may be heated to a temperature of between about 90 and about 180° C. In other embodiments, the plant source may be heated to a temperature of between about 90 and about 175° C., between about 90 and about 170° C., between about 90 and about 165° C., or between about 90 and about 160° C. In some other embodiments, the plant source may be heated to a temperature of between about 125 and about 180° C., between about 130 and about 180° C., between about 135 and about 180° C., or between about 140 and about 180° C. In other embodiments, the plant source may be heated to a temperature of between about 125 and about 170° C., between about 130 and about 165° C., or even between about 135 and about 160° C.

Heating at lower temperatures is also contemplated, mainly to avoid the risk of burning the plant source. However, in cases where lower temperatures are used, longer heating periods should be applied. In addition, heating may be carried out in two stages; a first stage for drying the water from the plant (50-70° C. for up to 120 min) and a second stage at 70-160° C. for decarboxylation.

In some embodiments, heating may be carried out under a nitrogen (preferably oxygen-free) atmosphere.

In some embodiments, the plant source may be heated for a period of time of between about 5 and 240 minutes. In other embodiments, the plant source may be heated for a period of time of between about 10 and 100 minutes, between about the 15 and 80 minutes, or between 20 and 60 minutes.

Additional extraction of cannabinoids from the biomass slurry may be carried out by employing additional cycles of extraction, thereby maximizing the yield obtained from a given quantity of plant source. Namely, several consecutive extraction cycles may be carried out on the same plant sample by using fresh batches of extraction medium in order to maximize extraction of the desired cannabinoid from the plant source. Thus, in some embodiments, the process may further comprise:

(d) mixing the biomass slurry with a second quantity of extraction medium to obtain a second mixture;
(e) homogenizing the second mixture; and
(f) separating the second mixture into biomass slurry and highly cannabinoid-loaded medium.

In some embodiments, the step sequence (d)-(f) is repeated between 1 and 7 times.

In order to obtain a higher extraction load in the medium, the process may be carried out in several cycles of extraction by using a cannabinoid-loaded medium to extract additional quantities of the same cannabinoid from a new sample of plant source (that was not previously extracted). Thus, in some embodiments, the process may further comprise:

(d') mixing the cannabinoid-loaded medium with a second quantity of the plant source to obtain a second mixture;
(e') homogenizing the second mixture; and
(f') separating the second mixture into biomass slurry and highly cannabinoid-loaded medium.

In some embodiments, the step sequence (d')-(f') is repeated between 1 and 7 times.

The mixing, homogenizing and separating parameters of steps (d)-(f) or (d')-(f') may be the same or different than those describe hereinabove in connection with steps (a)-(c).

It both process sequences described herein, it is contemplated by some embodiments that fresh extraction medium and cannabinoid-loaded medium are used in different cycles of the process. Namely, some of the cycles may be carried out with fresh extraction medium, while other cycles in the same process sequence may be carried out with cannabinoid-loaded medium.

The spent biomass can be further processed by any desirable method to extract further components, such as THC, essential oils, terpenes and other active components of the plant source, etc.

Cannabinoid-loaded medium quotas from different extraction batches may be mixed together to obtain a desired concentration of the cannabinoid in a final product. Such mixing may be carried out by any suitable mixing method. The cannabinoid-loaded medium can be used as-is, or can be further formulated by addition of other components (antioxidants, preservatives) to be loaded into liquid-gel capsules, creams, gels, patches, etc., or diluted as further detailed below.

In another aspect of this disclosure, there is provided an extraction medium for selective extraction of a desired cannabinoid (e.g. cannabidiol (CBD)) from a cannabinoid-containing plant source, comprising at least one oil, at least one hydrophilic surfactant, and at least one solvent, the extraction medium optionally further comprising at least one phospholipid and/or at least one co-solvent.

In a further aspect, this disclosure provides a cannabinoid-loaded medium (e.g. CBD) obtained by the process described herein.

Yet a further aspect of this disclosure provides a CBD-loaded medium comprising at least 0.1 wt % CBD, at least one oil, at least one hydrophilic surfactant, and at least one co-surfactant, the medium optionally further comprising at least one solvent, at least one co-solvent, and/or at least one phospholipid.

In some embodiments, the CBD-loaded medium comprises between about 1 and 12 wt % CBD. In other embodiments, the CBD-loaded medium comprises at most 1 wt % of THC.

The oil, hydrophilic surfactant, solvent and phospholipid are selected from those described hereinabove.

In additional embodiments, each of the extraction medium described herein may additionally comprise at least one additive, selected from antioxidants (e.g. tocopherols), oxygen scavengers, anti-microbial preservatives, membrane-piercing agents (peptides), transmembrane penetrating enhancers (e.g. transcutol, isosorbide, oleic acid, propylene glycol, maltodextrines, cyclodextrines, etc.), flavoring agents and/or aromatic agents.

The cannabinoid-loaded media may be used as is, i.e. without addition of other components, as pharmaceutical compositions. Alternatively, the cannabinoid-loaded media of this disclosure may be formulated into various formulations, by diluting them with various aqueous liquids or by incorporating them into various other carriers. The concentrate, as well as the diluted form of this disclosure, greatly increases the stability of the formulation over time, reduces the risk of contamination, broadens the scope of its application to a great variety of concentrations (various doses) and diluted forms, while permitting the medical professionals the decision how, when and which concentration (dilution) to prepare prior to use.

The term concentrate denotes a substantially water-free, oil-based structured lipid/surfactants system, in which surfactant tails are solubilized by the CBD and the oil facilitating full dilution by a diluent aqueous phase (are dilutable) at will to form diluted cannabinoid-loaded medium for administration. In other words, the concentrates are designed for fast and complete dilution in a suitable diluent, typically water and aqueous solutions (such as sugar, sweetener solutions and water-alcohol mixtures), forming the diluted microemulsions, as will now be described. Upon dilution with a suitable diluent, the concentrate of the invention spontaneously forms microemulsions, which are at first "solvated domains (or clusters) of surfactant" mesophases that upon minor dilution (ca. 10-30 wt %) form water-in oil nanodroplets; and upon further dilution transform to bicontinuous mesophases and into oil-in-water (O/W) nanodroplets, in which the diluent forms the continuous phase, while the oil phase is in the form of discrete droplets of nanometric size (i.e. the diluted microemulsions). As noted above, the diluted cannabinoid-loaded media are formed from the concentrate spontaneously, namely without the need to apply any shear, cavitation or homogenization processes.

In addition to providing flexibility in formulating and better control of the cannabinoids' profile administration dose, the concentrates produced by the process described herein are substantially free, i.e. devoid, of water. Once water is absent from the extraction medium, the concentrates lack the environment sustaining microorganisms growth (e.g. fungi or bacteria), permitting longer storage without (or with minimal) risk of contamination. Without wishing to be bound by theory, one of the reasons due to which almost no bacterial contamination is observed for such concentrates may be the absence of unbound water, thereby limiting microbial growth and substantially extending the shelf life of the cannabinoid-loaded medium.

In some embodiments, the cannabinoid-loaded medium (i.e. concentrates) are entirely devoid of water.

The ratio between the concentrate and the diluent depends on the desired final concentration of cannabinoids in the extraction medium. According to some embodiments, the diluted cannabinoid-loaded medium comprises between about 60 and about 98 wt % of the diluent.

In another aspect, the present disclosure provides a pharmaceutical or nutraceutical composition comprising the cannabinoid-loaded medium as described herein.

In some embodiments, the pharmaceutical composition may comprise at least one pharmaceutically acceptable carrier. The "pharmaceutically acceptable carriers" described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the active agent (i.e. cannabinoids profile), as well as by the particular method used to administer the composition. Accordingly, there is a wide variety of suitable formulations of the pharmaceutical composition of the present invention.

As described above, when diluted with an aqueous liquid, a spontaneous oil-in-water (O/W) nano-micelles are formed, in which the diluent forms the continuous phase, while the oil phase is in the form of discrete droplets of nanometric size. In some embodiments, the oil droplets of the diluted medium may have an average droplet diameter of at most 100 nanometers (preferably <50 nm).

In some other embodiments, the droplets size is between about 10 and 50 nm (nanometers). The droplet size refers to the arithmetic mean of measured droplets' diameters, wherein the diameters range ±15% from the mean value.

Further, diluted media of the present disclosure are characterized by a mono-disperse size distribution of the oil droplets. Namely, the size distribution of the oil droplets is narrow, without significant divergence from the mean size value. In some embodiments, the polydispersity index (PDI) of the distribution of oil droplets is between about 0.03 and 0.1.

The aqueous diluent may be selected from water, flavored water, water for injection, saline, dextrose solution, or a buffer having a pH between 3 and 9. Flavoring and/or aromatic agents may be added during or after dilution.

The pharmaceutical composition may comprise a variety of additional components, depending on the administration route and/or desired properties of the formulation, such as aqueous and non-aqueous diluents, isotonic sterile injection solutions, anti-oxidants, buffers, bacteriostats, suspending agents, solubilizers, thickening agents, gelling agent, emollients, moisturizers, stabilizers, preservatives, buffers, coloring agents, a fragrance, absorbers, filters, electrolytes, proteins, chelating agents, and others.

In some embodiments, the pharmaceutical composition is in a form selected from a gel, a lotion, oil, soap, a spray, an emulsion, a cream, an ointment, capsules, soft-gel capsules, chewing gum, a topical patch, buccal or sublingual film, ophthalmic drops or a solution.

In other embodiments, the composition may be adapted for delivery of the cannabinoid in various routes of administration, including topical, oral, rectal, vaginal, buccal, nasal, transdermal, subcutaneous, intravenous, intramuscular, intranasal, by inhalation, occularly or parenterally (intravenous (iv), intramuscular (im), and subcutaneous (sc)) into the circulatory system of a subject.

Formulations suitable for oral administration can consist of (a) liquid solutions, such as an effective amount of the compound, or composition comprising same, dissolved in diluents, such as water, saline, flavored water, or juice (e.g. orange juice); (b) capsules, sachets, tablets, lozenges, and troches, each containing a predetermined amount of the active ingredient, as solids or granules; (c) powders; (d) suspensions in an appropriate liquid; and (e) concentrates or diluted systems (f) oral, nasal, sublingual or buccal spray (g) inhalation spray. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active formulation in an inert base, such as gelatin and glycerin, or sucrose and acacia, emulsions, gels, and the like containing, in addition to the active formulation, such carriers as are known in the art.

Another aspect of the invention provides an extraction medium or a pharmaceutical composition of this disclosure, for use in treating a condition selected from pain associated disorders (as an analgesic), inflammatory disorders and conditions (as anti-inflammatory), apatite suppression or stimulation (as anoretic or stimulant), symptoms of vomiting and nausea (as antiemetic), intestine and bowl disorders, disorders and conditions associated with anxiety (as anxiolytic), disorders and conditions associated with psychosis (as antipsychotic), disorders and conditions associated with seizures and/or convulsions (as antiepileptic or antispasmodic), sleep disorders and conditions (as anti-insomniac), disorders and conditions which require treatment by immunosuppression, disorders and conditions associated with elevated blood glucose levels (as antidiabetic), disorders and conditions associated with nerve system degradation (as neuroprotectant), inflammatory skin disorders and conditions (such as psoriasis), disorders and conditions associated with artery blockage (as anti-ischemic), disorders and conditions associated with bacterial infections, disorders and conditions associated with fungal infections, proliferative disorders and conditions, disorders and conditions associated with inhibited bone growth, post trauma disorders and others.

A further aspect, provides a method of treating a subject suffering from a condition, the method comprising administering to the subject an effective amount of the extraction medium or the pharmaceutical composition of this disclosure.

In some embodiments, the condition may be selected from those described hereinabove.

The extraction medium produced by the process described herein may be used as such to induce at least one effect, e.g., therapeutic effect, or may be associated with at least one agent, e.g., therapeutic agent, which is capable of inducing, enhancing, arresting or diminishing at least one effect, by way of treatment or prevention of unwanted conditions or diseases in a subject. The at least one agent (substance, molecule, element, compound, entity, or a combination thereof) may be selected amongst therapeutic agents, i.e. agents capable of inducing or modulating a therapeutic effect when administered in a therapeutically effective amount, and non-therapeutic agents, i.e. which by themselves do not induce or modulate a therapeutic effect but which may endow the pharmaceutical composition with a selected desired characteristic.

The pharmaceutical compositions of the present disclosure may be selected to treat, prevent or ameliorate any pathology or condition. The term treatment or any lingual variation thereof, as used herein, refers to the administering of a therapeutic amount of the composition or system described herein, whether in an concentrated extraction medium form or in a diluted form, which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease from occurring or a combination of two or more of the above.

As known, the effective amount for purposes herein may be determined by such considerations as known in the art. The effective amount is typically determined in appropriately designed clinical trials (dose range studies) and the person versed in the art will know how to properly conduct such trials in order to determine the effective amount. As generally known, the effective amount depends on a variety of factors including the distribution profile within the body, a variety of pharmacological parameters such as half-life in the body, on undesired side effects, if any, on factors such as age and gender, and others.

The term "subject" refers to a mammal, human or non-human.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between. It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

As used herein, the term "about" is meant to encompass deviation of ±10% from the specifically mentioned value of a parameter, such as temperature, pressure, concentration, etc.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Effect of Plant Pre-Heating

As explained hereinabove, at least a portion of the CBD is found in the plant in the form of CBDA. Decarboxylation of CBDA can be carried out by heating the plant at controlled conditions to obtain the desired CBD. The plants used in the following examples were various hybrids of *Cannabis sativa* and *Cannabis indica*.

For evaluating the effect of heating the plant source prior to the extraction process on the extraction yield, the content of cannabinoid species in various strains of dried cannabis plants were profiled prior to heating by HPLC.

Plant samples (a mixture of flowers, leaves and stems was used) were roughly chopped and heated in air atmosphere at a temperature of between 90 and 170° C. for between 10 and 120 minutes. The samples were then extracted with ethanol (10 ml per 100 mg of plant) for 30 minutes under stirring at 30-35° C. Ethanol was used as a solvent for a reference to the conversion of CBDA to CBD, as determined by HPLC. The sample was then filtered through cotton wool to obtain an extract, which was analyzed by HPLC.

HPLC analysis was carried out by using the following conditions: C18 column, mobile phase-gradient of methanol/water (69/31 v/v %) to 100% methanol, flow rate 0.3 ml/min.

Figure 1:
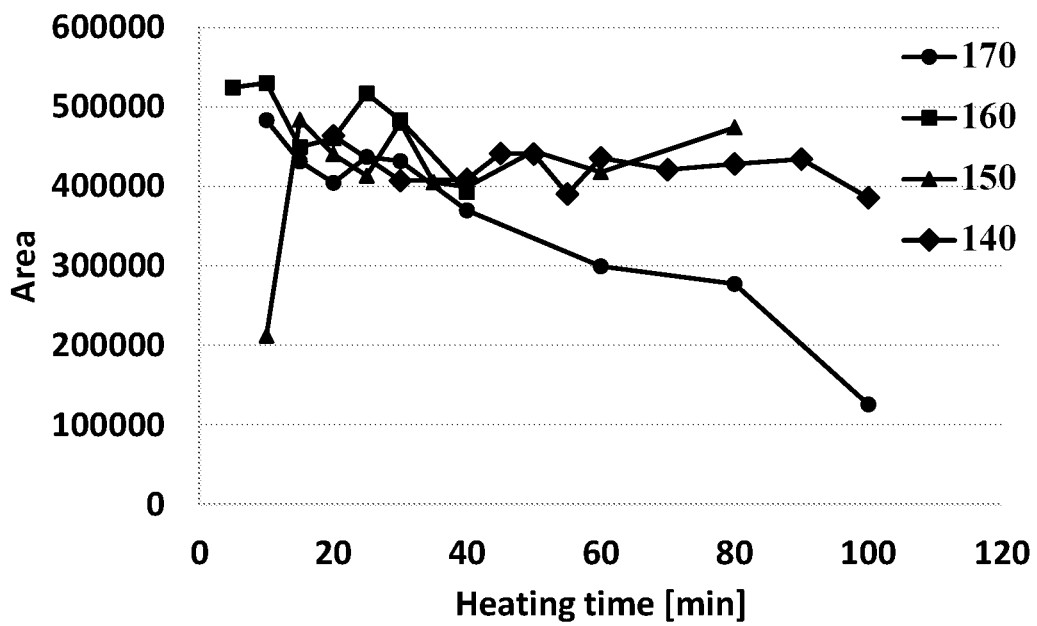
FIG. 1 shows CBD peak areas against heating temperature for plant samples heated at various temperatures for transforming CBDA to CBD as obtained by HPLC analysis.
Figure 2:
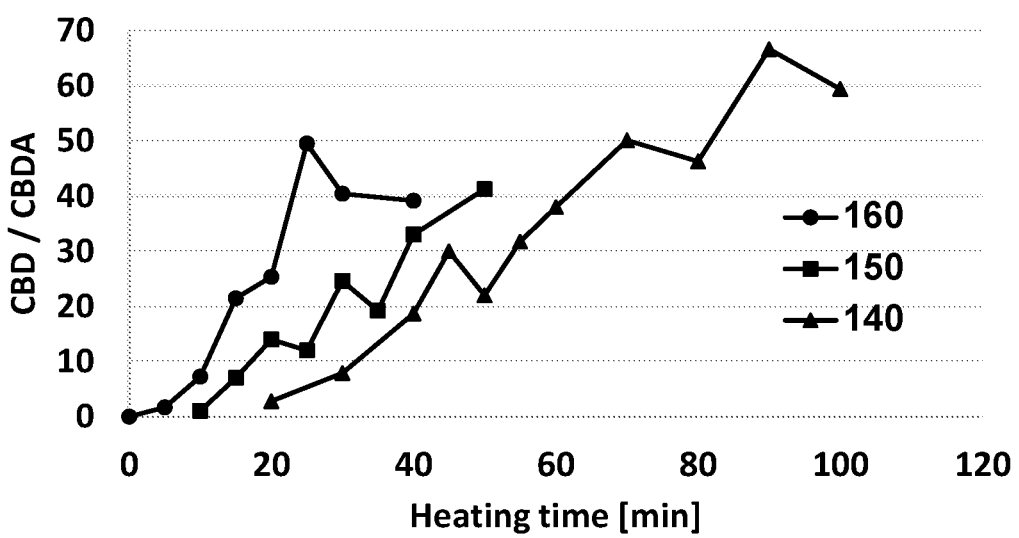
FIG. 2 shows CBD/CBDA peak areas ratio as obtained by HPLC analysis plotted against heating time at various heating temperatures.

CBD peak areas were plotted against heating temperature (FIG. 1). FIG. 2 presents the ratio between CBD and CBDA peak areas against heating time at various heating temperatures.

As evident from the results, heating increases significantly the concentration of CBD in the plant sample, thereby increasing the content of the desired extractable cannabinoid specie in the samples. When the samples were heated at a lower temperature range (140° C.), maximum CBDA-to-CBD transformation was observed after 60-90 minutes of heating. For higher temperatures (160° C.), 10-25 minutes of heating were sufficient to obtain desired levels of CBD in the samples.

Long heating at 140° C. (for 60-90 min) or short heating at 160° C. (for 10-25 min) are suitable for reaching the highest amount of CBD in the plant as well as high conversion of CBDA to CBD. Above 170° C. no CBDA was identified after already 10 min, however degradation products appear at early stages.

Thus, all the following extraction were done, based on these results, with plants that were heated at 160° C. for 15 min.

Extraction Medium and Preparations

As noted above, the extraction media used for the extraction process are self-assembled systems which are formed in a spontaneous manner. Therefore, several compositions of the extraction media were prepared by simple mixing of ingredients at 25-70° C. An exemplary process for preparing the extraction medium involves mixing together the oil, the surfactant and the co-surfactant (and where applicable also a solvent, a co-solvent and/or a phospholipid) until a homogenous, clear (transparent) mixture is obtained. In case the surfactants or oil are solid at room temperature, heating can be applied while mixing to allow full dissolution and formation of the empty extraction medium.

The extraction medium is then slowly added to the pre-heated and chopped plant to allow appropriate wetting and then mixed and homogenized. Another variation of the process includes adding solid plant parts (leaves or buds for examples) stepwise to the empty (un-loaded) extraction medium until a homogeneous slurry is obtained.

Extraction was carried out under heating with our without inert atmosphere, thereby solubilizing CBD into the extraction medium. The mixture was allowed to settle to the bottom of the mixing vessel before filtration and/or centrifugation.

Table 1 provides details of exemplary formulations used in the process of the present disclosure.

TABLE 1

Formulations of extraction medium

| | Formulation 5CS | | Formulation AX1 | |
|---|---|---|---|---|
| | Component | wt % | Component | wt % |
| Oil | MCT | 3.6 | R-(+)-Limonene | 5 |
| Hydrophilic surfactant | Polysorbate 80 (Tween 80) | 35.37 | Polysorbate 80 (Tween 80) | 45 |
| | Cremophor EL castor oil* | 42.57 | | |
| Co-surfactant | Propylene glycol (PG) | 8.46 | Propylene glycol (PG) | 45 |
| Solvent | — | — | Ethanol | 5 |
| Phospholipid | Phosal 50 PG** | 10 | — | — |

*Polyoxyl 35 castor oil
**Phosal 50 PG composed of 1.5-2.5% wt ethanol, >500 ppm ethylenemethylketone, 0.5 wt % water, 33.8-41.2 wt % propylene glycol, <50.0 wt % phosphatidylcholine, >6 wt % lyso-phosphatidylcholine The formation of commonly known emulsions, which are typically a dispersion of two immiscible liquids formed in the presence of emulsifiers, are based on the reduction of the interfacial tension between the two phases such that the dispersed droplets are covered by an emulsifier's layer to retard aggregation, flocculation, coalescence and phase separation. Since emulsifiers do not reduce the interfacial tension to zero and the coverage is not complete, emulsions require application of relatively high shear forces of multistage homogenizer to reduce the droplets size upon preparation of the emulsion. The resulting non-uniform droplets have a strong tendency to coalesce and/or result in phase-separate, thereby stabilizing the system energetically. Thus, emulsions show a relatively non-uniform and large droplet size, which are unstable over prolonged periods of time (i.e. the droplet size increases due to coalescence or can even result in phase separation). Moreover, in a typical emulsion the droplet size is far from being homogenous, resulting in milky, white-opaque appearance. Extraction with an emulsion media leads to very fast phase separation and very limited amount of extraction load.

Contrary to known emulsions, the extraction media used in the process of disclosed herein have zero interfacial tension, and therefore are spontaneously formed as energetically balanced systems, which are characterized by a small and uniform droplet size, resulting in transparent systems. Due to their energetic balance, the extraction media used in the process (and as a result also the cannabinoid-loaded medium) are stable for prolonged periods of time, maintain their droplet size and size uniformity also upon dilution with aqueous liquids, making them suitable for formulation into various pharmaceutical compositions and enabling their administration in a variety of administrations routes and forms.

Additional exemplary formulations are detailed in Table 2.

TABLE 2

Formulations of extraction medium

| | Formulation OR103(2) slow release | | Formulation OR210SE | |
|---|---|---|---|---|
| | Component | wt % | Component | wt % |
| Oil | Triacetin | 5 | MCT | 5 |
| Hydrophilic surfactant | Labrasol | 25 | L-1695- sucrose mono/dilaurate | 60 |
| | Cremophor EL castor oil* | 35 | | |
| Co-surfactant | Propylene glycol (PG) | 20 | Propylene glycol (PG) | 20 |
| Solvent | Isopropyl alcohol (IPA) | 5 | Isopropyl alcohol (IPA) | 5 |
| Phospholipid | Phosal 50 PG* | 10 | Phosal 50 PG* | 10 |

Figure 3:
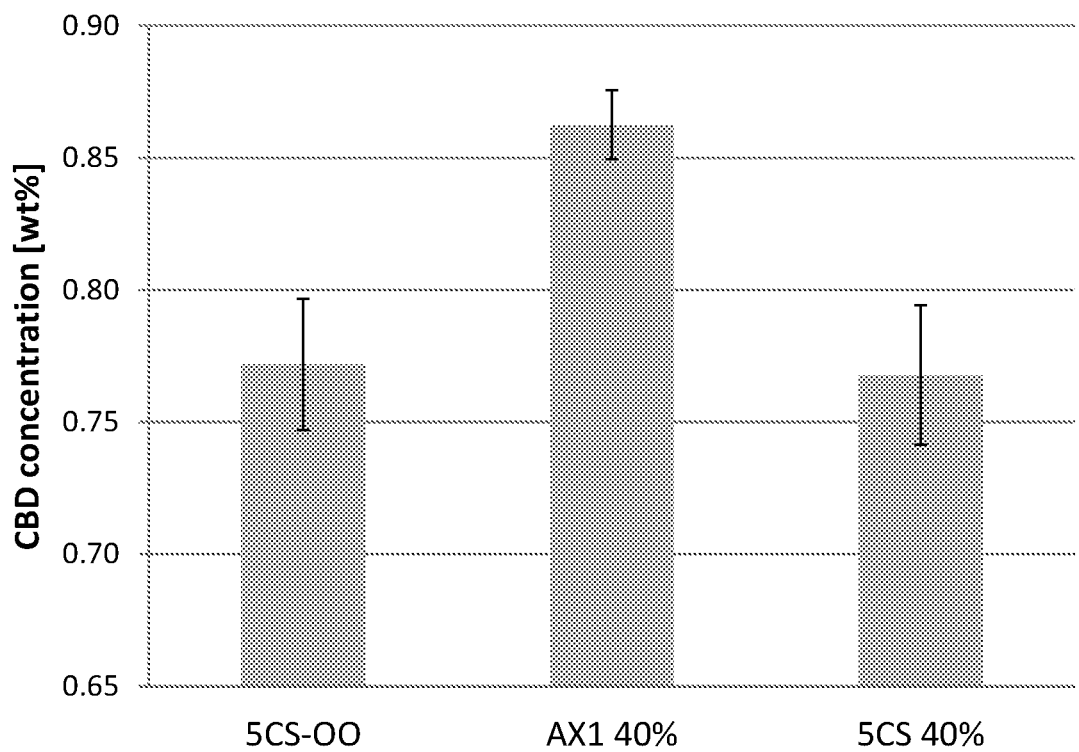
FIG. 3 shows CBD concentration in the extraction medium and in 40% water-diluted extraction media.

*Phosal 50 PG composed of 1.5-2.5% wt ethanol, >500 ppm ethylenemethylketone, 0.5 wt % water, 33.8-41.2 wt % propylene glycol, <50.0 wt % phosphatidylcholine, >6 wt % lyso-phosphatidylcholine The ability of formulations comprising olive oil instead of MCT (as the oil component in the extraction medium of formulation 5CS), as well as the ability of diluted media (40 wt % water) to extract CBD from a plant source was also evaluated. As seen in FIG. 3, olive oil is also suitable as an oil component in the extraction media. Further, diluted media also show the capability of extracting CBD form the plant material, and even show CBD concentrations slightly higher compared to the concentrated formulation.

Extraction of CBD from Plant Samples by Extraction Media

Cannabinoid Profile of Plant Samples

Various strains of cannabis were tested in the extraction process of the present disclosure. Samples of the plants were evaluated for cannabinoids profiles prior to extraction with the extraction medium by ethanol extraction (as described above) and HPLC analysis. The cannabinoids profiles of the various strains are provided in Table 3.

TABLE 3

Cannabinoids profile of some strains

| Strain  | CBVD (%) | CBG (%) | CBD (%) | $\Delta^9$-THC (%) | CBN (%) |
|---------|----------|---------|---------|--------------------|---------|
| M1      | —        | —       | —       | 1.1                | Trace   |
| M1-L    | 0.5      | 0.1     | 6.7     | 0.7                | Trace   |
| M(1)-1  | 0.2      | 1.7     | 12.3    | 0.6                | Trace   |
| M(1)-3  | 0.5      | 0.2     | 10.6    | 0.5                | Trace   |
| M(3)-1  | 0.8      | 0.1     | 11.0    | 0.5                | Trace   |
| M(3)-2  | 0.6      | 0.1     | 9.4     | 0.4                | Trace   |

All extraction medium processes described herein were carried out on plant samples heated at 160° C. for 15 minutes. All of the following experiments were carried out on M(1)-1 strain.

Effect of Extraction Duration

Plant samples (after heating) were mixed with AX-1 extraction medium at a weight ratio of 1:40. The mixtures were then homogenized at room temperature using lab Silverson homogenizer L5M-A for 30 minutes. After homogenization, each sample was centrifuged at 4000 rpm for 20 minutes or filtered through cotton wool. Samples were prepared in triplicates.

Figure 4:
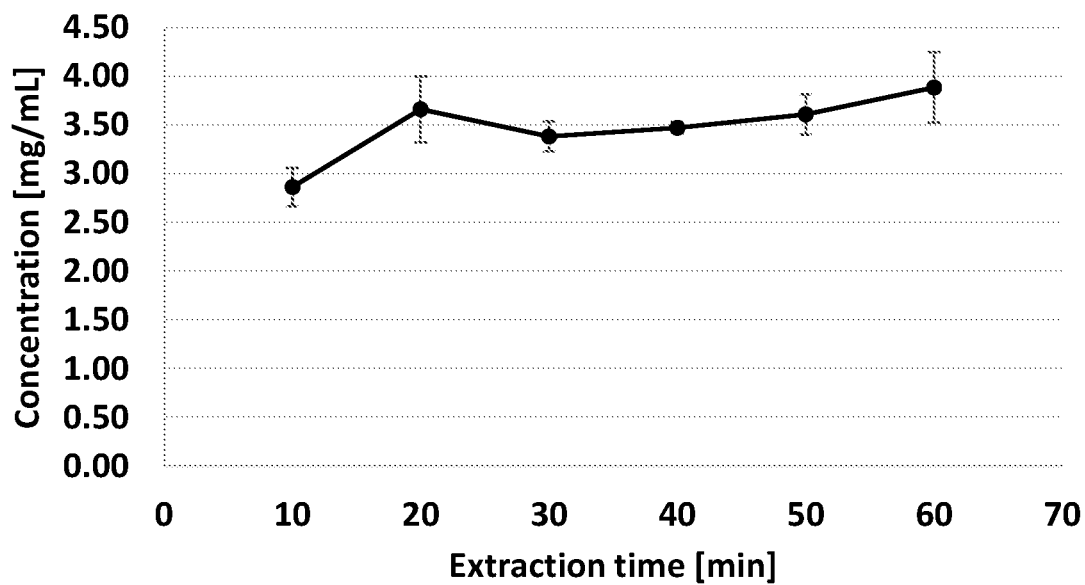
FIG. 4 shows CBD concentration in the AX-1 extraction medium as a function of extraction duration.
Figure 5:
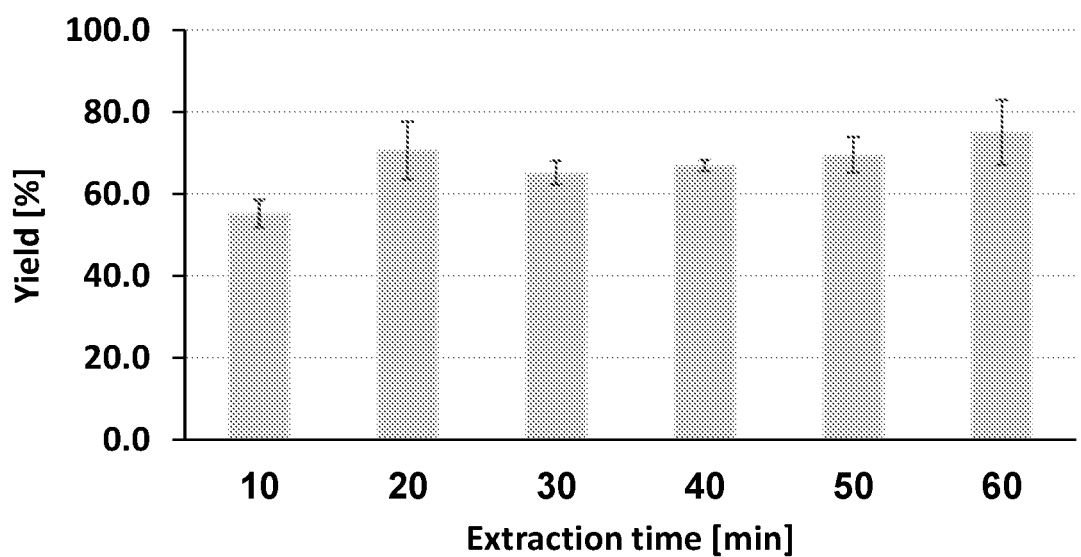
FIG. 5 shows the yield of CBD extraction from the plant using AX-1 extraction medium as a function of extraction duration.

Analysis of cannabinoids content in the extracts was carried out by HPLC vis-à-vis calibration curves. FIGS. 4 and 5 show the concentration of CBD in the extracts and the extraction yield, respectively, as a function of the extraction time. The ratio between the CBD peak area and those of other cannabinoids in the plant sample (CBDA, THC and CBN) are shown in FIG. 6.

As can clearly be seen from the results, the extraction medium is highly selective towards CBD. After one round of extraction, the medium contains at least 35-folds CBD compared to THC and selectivity is reduced as the extraction time increases. The ratio of CBD to CBDA starts from 27:1 and drops to at least 14-folds CBD compared to CBDA. This suggest that extraction of the plant source with extraction media as described herein may be used to obtain CBD-rich products with significantly lower concentrations of THC compared to other commercially available products.

As observed from FIG. 4, a plateau is reached after 20 min of extraction. Beyond the 20 min no significant increasing in CBD concentration or extraction yield is achieved. Further, as seen from FIG. 5, a single extraction process yielded extraction of between 55 and 75% of CBD from the plant source. For those reasons a duration of 30 min was chosen for the following extractions.

Figure 6:
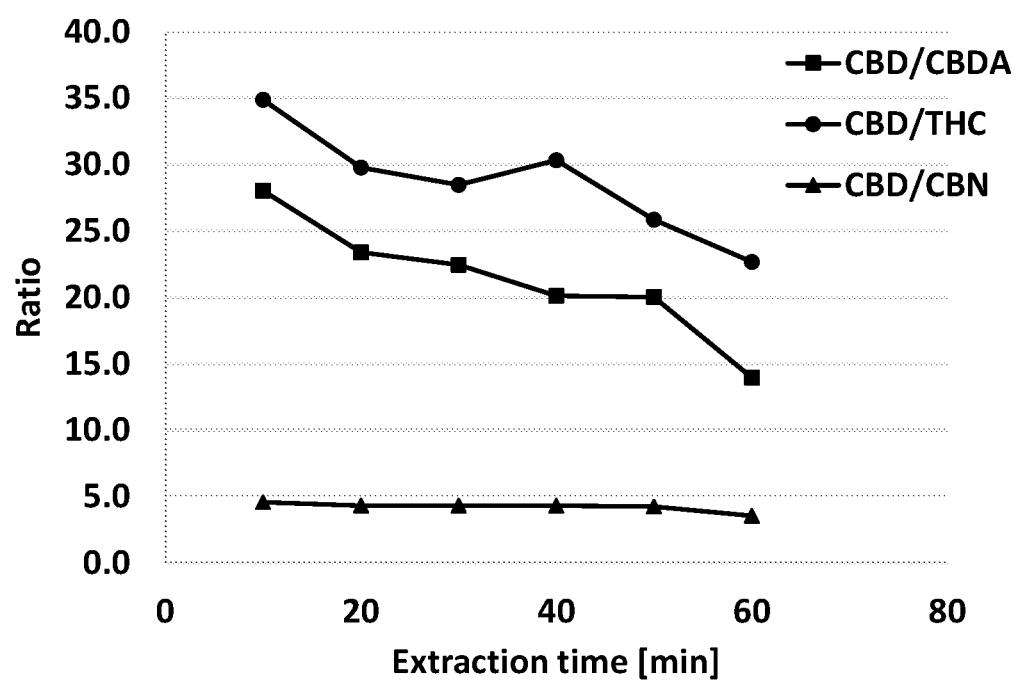
FIG. 6 shows the ratio between the CBD peak area and the peak areas of other cannabinoids in the plant sample (CBDA, THC and CBN) for various extraction durations.

As seen in FIG. 6, Examining the ratio of CBD to other cannabinoids shows that the longer the extraction the lower the ratio, which means that extra time allows another cannabinoid to be extracted more rapidly compared to the CBD.

Effect of Plant-to-Microemulsion Ratio

The effect of the plant-to-medium ratio on the extraction efficiency was assessed by analyzing mixtures of varying plant source to extraction medium ratios.

Plant samples (after heating) were mixed with AX-1 extraction medium at a weight ratio of between 1:15 and 1:60 (plant:medium). The mixtures were then homogenized at room temperature using Silverson homogenizer for 30 minutes. After homogenization, each sample was centrifuged at 4000 rpm for 20 minutes or filtered through cotton wool. Samples were prepared in triplicates.

Figure 7:
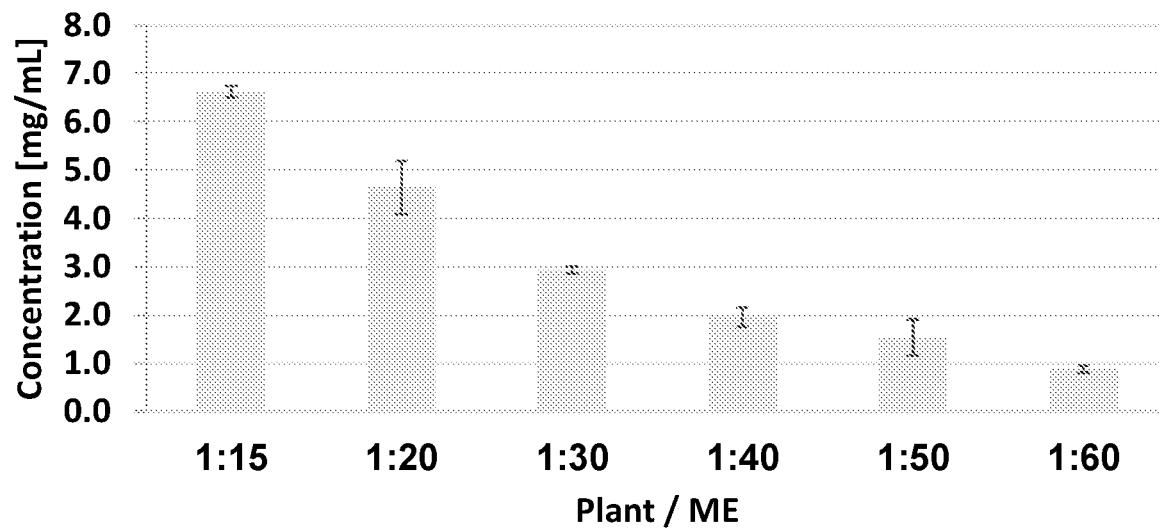
FIG. 7 shows CBD concentration in the AX-1 extraction medium as a function of plant-to-medium ratio.
Figure 8:
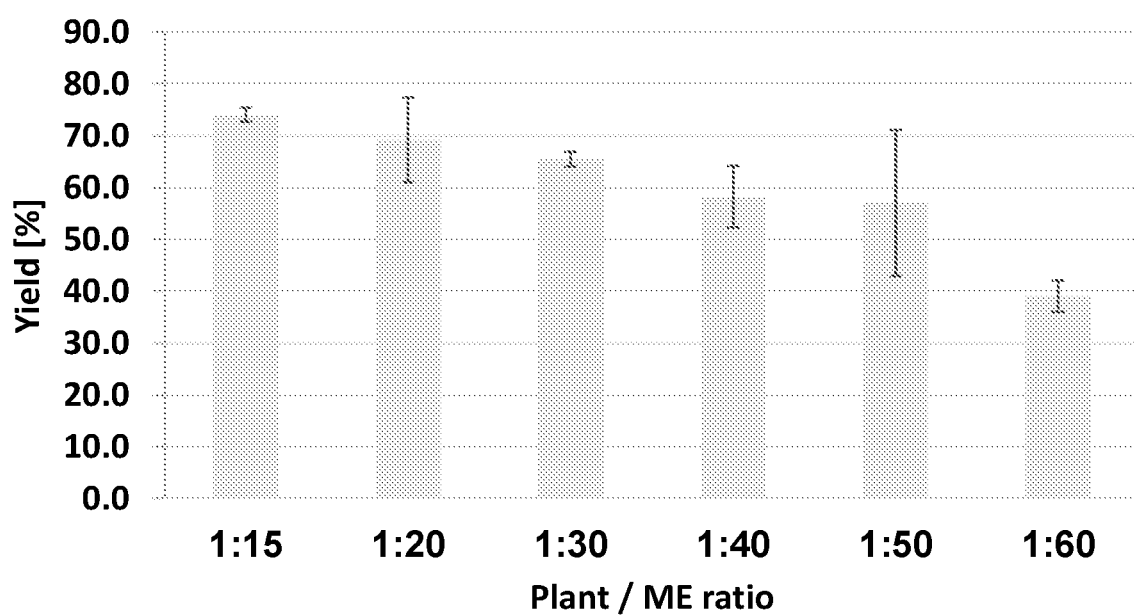
FIG. 8 shows the yield of CBD extraction from the plant using AX-1 extraction medium as a function of plant-to-microemulsion ratio.
Figure 9:
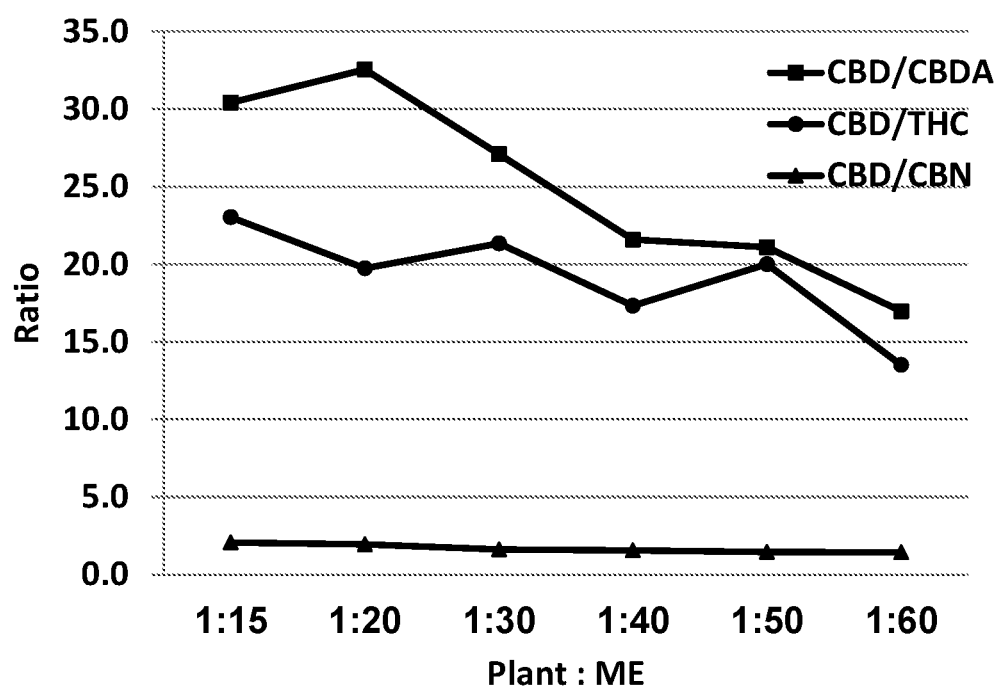
FIG. 9 shows the ratio between the CBD peak area and the peak areas of other cannabinoids in the plant sample (CBDA, THC and CBN) for various plant-to-medium ratios.

Analysis of CBD content in the extracts was carried out by HPLC vis-à-vis a calibration curve. FIGS. 7 and 8 show the concentration of CBD in the extracts and the extraction yield, respectively, as a function of the plant-to-medium ratio. The ratio between the CBD peak area and those of other cannabinoids in the plant sample (CBDA, THC and CBN) are shown in FIG. 9.

Although the extraction yields decreases upon increasing the plant:medium ratio, in all weight ratios the selectivity of extraction is evident. The selectivity is controlled by the preference of the CBD molecule to interact with the surfactants tails and system core in comparison to the THC molecule, with a predominant factors being the polarity and structure of the molecule. This suggests that selective extraction of various cannabinoids may be tailored by varying the polarity of the extraction medium.

Multiple-Extractions Process

Increasing the CBD concentration in the extraction medium was carried out by a multi-extraction process. For the multi-extraction process a number of extraction cycles are carried out by using the same quota of extraction medium for several extraction cycles, in each cycle a fresh sample of plant is extracted according to the following procedure.

A heated plant sample was mixed with AX-1 extraction medium at a weight ratio of 1:15. The mixture was then homogenized at room temperature using Silverson homogenizer for 30 minutes. After homogenization, the sample was centrifuged at 4000 rpm for 20 minutes or/and filtered through cotton wool. After separating the CBD-loaded medium from the spent biomass, the CBD-loaded medium was weighed and a new sample of plant was added at a weight ratio of 1:15 (plant:medium). Homogenization and separation were carried out for the new mixture. Two additional such cycles of extraction were carried out, amounting to a total of 4 extraction cycles. A total of 3 multi-extraction processes were carried out.

Samples of the medium were taken in between cycles to assess the effect of the number of cycles on the cannabinoids profile and CBD loading of the medium.

Figure 10:
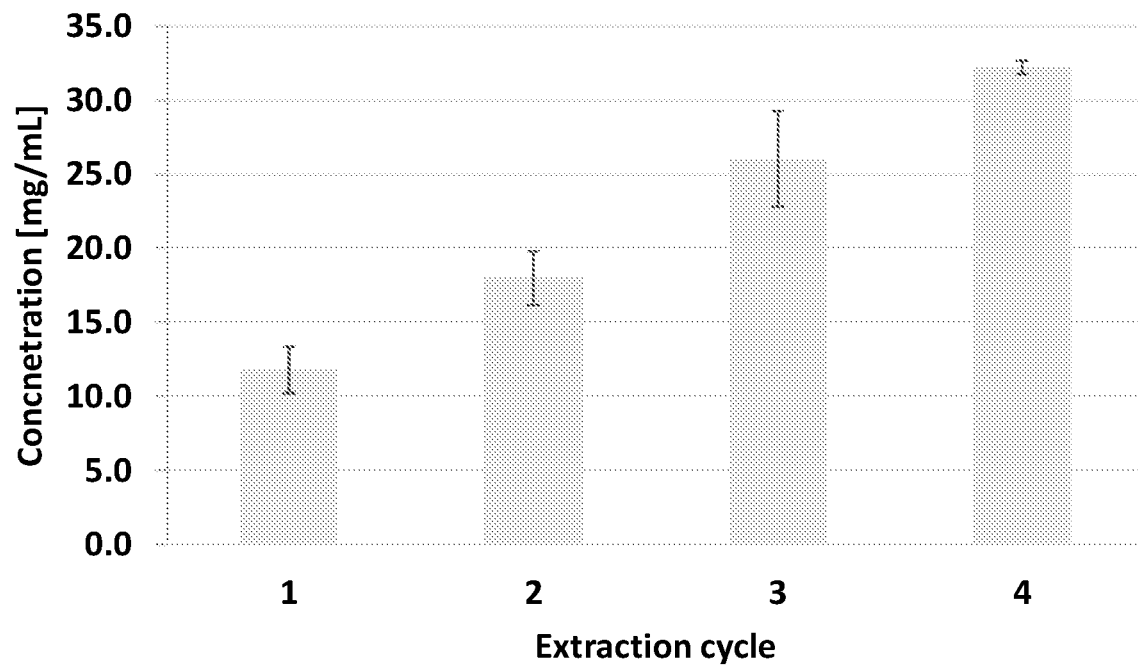
FIG. 10 shows CBD concentration in the AX-1 extraction medium as a function of the number of extraction cycles.
Figure 11:
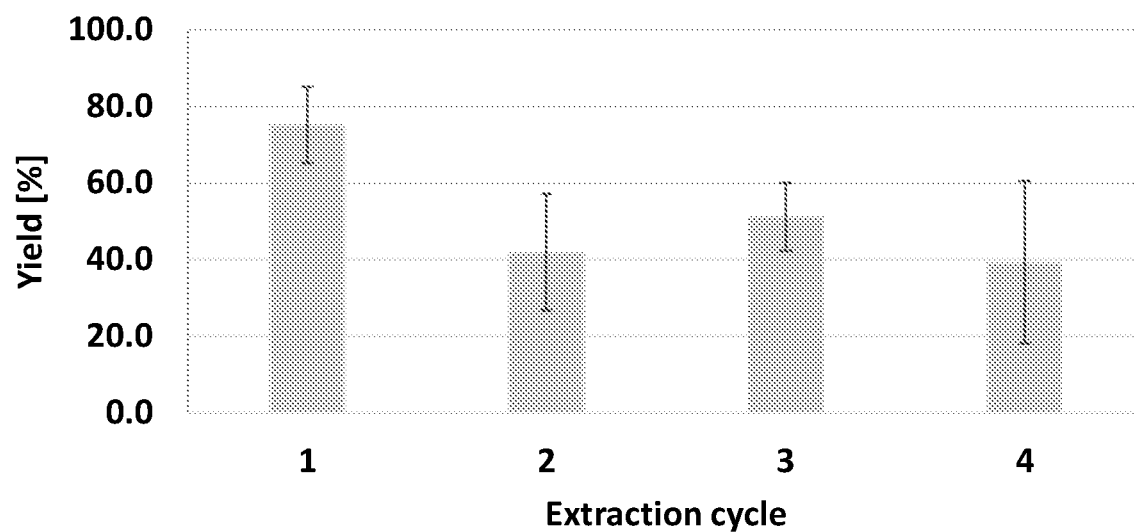
FIG. 11 shows the yield of CBD extraction from the plant using AX-1 extraction medium as a function of the number of extraction cycles.
Figure 12:
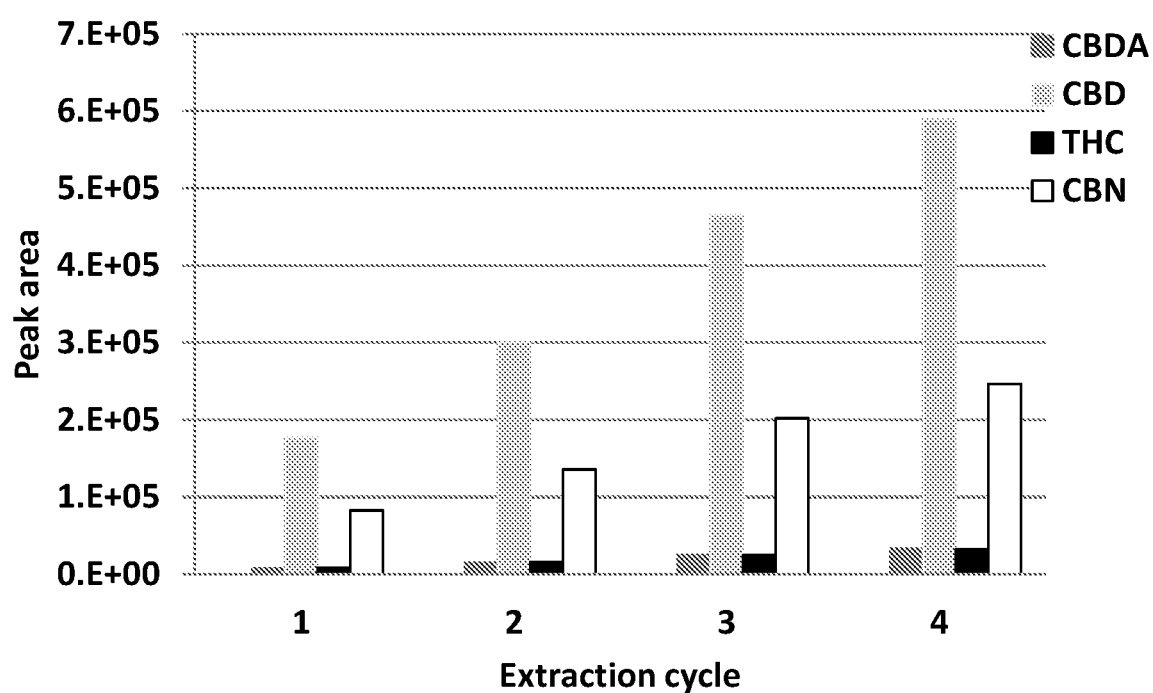
FIG. 12 shows the peak areas for CBD, CBDA, THC and CBN in the extraction medium samples as function of the number of extraction cycles.

Analysis of CBD content was done according to the description hereinabove. FIGS. 10 and 11 show the concentration of CBD in the extracts and the extraction yield, respectively, as a function of the number of extraction cycles. The content of the various cannabinoids in the samples is shown in FIG. 12.

As evident from the results, the CBD content in the extraction medium increases by at least 2-folds as a result of the multi-extractions process. However, as the extraction medium becomes loaded with CBD, the extraction efficiency of the extraction medium decreases compared to the extraction efficiency at the first cycle of extraction due to the proximity of the CBD content to the maximum loading capacity of the extraction medium. Regardless of this decrease, the selectivity of extraction is maintained throughout the process cycles.

Reference Extraction Media

To demonstrate the selectivity of the extraction media described herein towards specific cannabinoids, and especially towards the extraction of CBD, plant samples were also extracted with either ethanol or petroleum ether. Both solvents are known and used to extract cannabinoids. The process of extraction was identical to that carried out with the extraction medium of the present disclosure, as described above.

Figure 13:
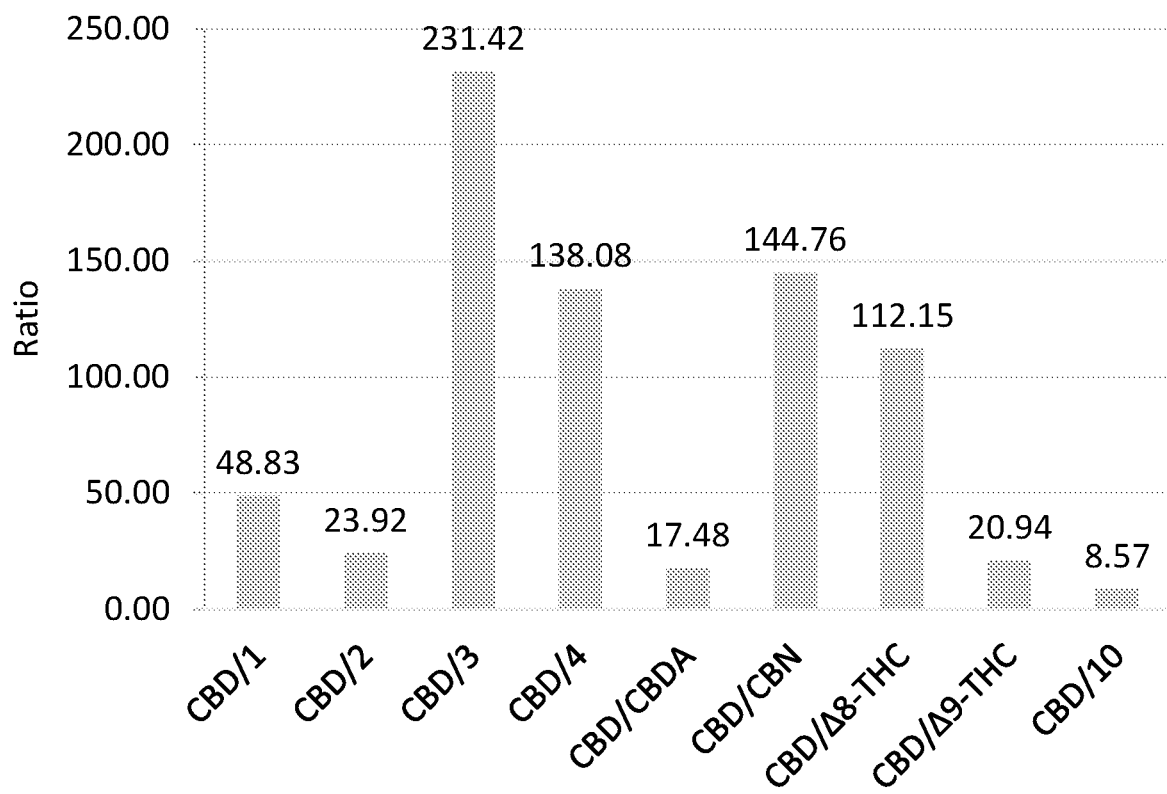
FIG. 13 shows the extraction concentration and yield of CBD and other cannabinoids using ethanol.
Figure 14:
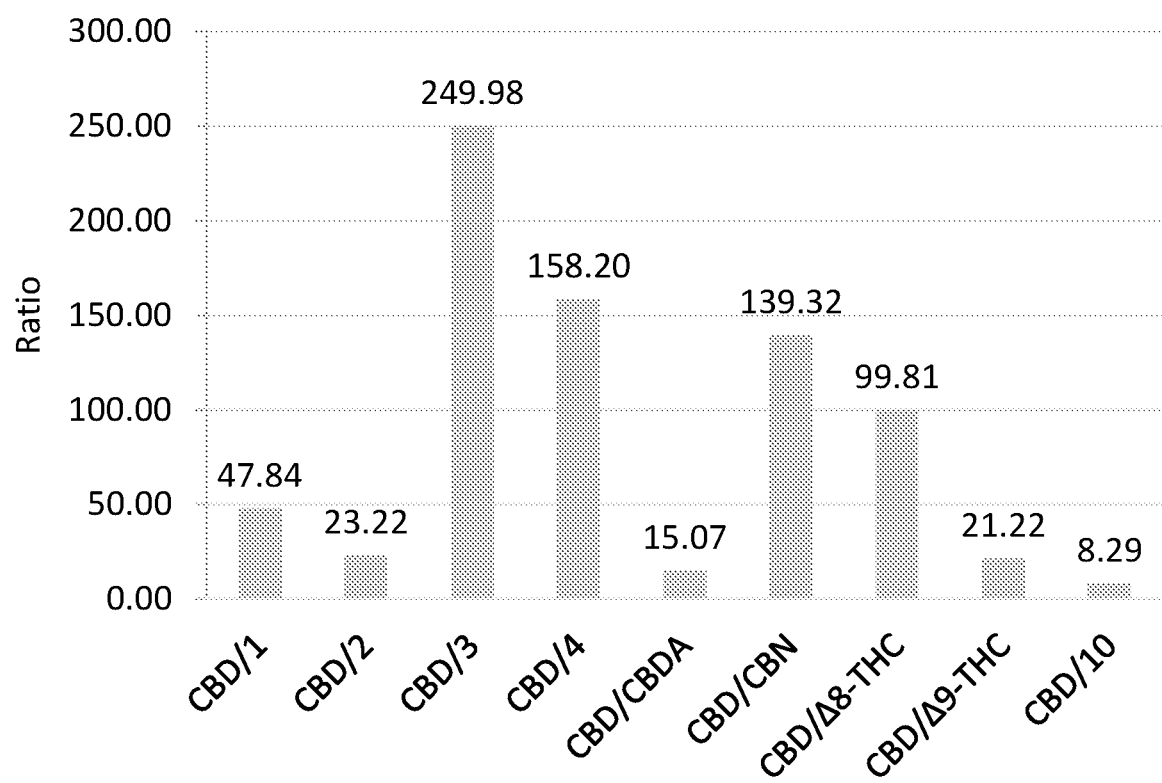
FIG. 14 shows the extraction concentration and yield of CBD and other cannabinoids using petroleum ether.

The results are provided in FIGS. 13-14, which show the quantities ratio between CBD and other extracted cannabinoids, as determined by HPLC.

As can clearly be seen, extraction carried out in both ethanol and petroleum ether showed a CBD:THC ratio of at most 22:1, while extraction with the extraction medium showed CBD:THC ratios of ~35:1. Namely, the extraction media described herein provides high selectivity to the extraction of CBD over other cannabinoids, enabling obtaining an extraction product with extremely low levels of THC.

Further, the lading capacity of CBD in the extraction medium is significantly higher than that obtained for either ethanol or petroleum ether, as can be seen in Table 4, attesting to the ability of the extraction medium to quantitatively extract CBD from the plant source.

TABLE 4 comparative CBD loading of extraction medium vs. ethanol and petroleum ether

| Extraction process | CBD loading (mg/ml) |
|---|---|
| AX-1 | >6* |
| Ethanol | 1.2 |
| Petroleum ether | 0.9 |

*after 1 extraction cycle. Up to 22 mg/ml were obtained after 4 extraction cycles Stability of Formulations 5CS and AX2 extraction media (see Table 5-1) were loaded with 5 wt % CBD and incubated at three different temperature (4, 25 and 40° C.) under different conditions (without protection, with the addition of 600 ppm α-tocopherol acetate and under nitrogen atmosphere). Both the concentrate and a diluted microemulsion (80% water) were tested.

TABLE 5-1

Formulations of microemulsions for stability tests

| | Formulation 5CS | | Formulation AX2 | |
|---|---|---|---|---|
| | Component | wt % | Component | wt % |
| Oil | MCT | 3.6 | MCT | 5 |
| | | | Oleic acid | 2 |
| Hydrophilic surfactant | Polysorbate 80 (Tween 80) | 35.37 | Polysorbate 80 (Tween 80) | 35 |
| | Cremophor EL castor oil* | 42.57 | Cremophor EL castor oil* | 32 |
| | | | Glycerol | 6.5 |
| Co-surfactant | Propylene glycol (PG) | 8.46 | Propylene glycol (PG) | 9 |
| Solvent | — | — | Ethanol | 5.5 |
| Phospholipid | Phosal 50 PG** | 10 | Phosphatidylcholine | 5 |

*Polyoxyl 35 castor oil
**Phosal 50 PG composed of 1.5-2.5% wt ethanol, >500 ppm ethylenemethylketone, 0.5 wt % water, 33.8-41.2 wt % propylene glycol, <50.0 wt % phosphatidylcholine, >6 wt % lyso-phosphatidylcholine The visual appearance of the samples were recorded after 30 days of incubation. The results are detailed in Table 5-2.

TABLE 5-2

Stability of CBD-loaded media

| | Incubation | 5CS | | AX2 | |
|---|---|---|---|---|---|
| Extraction Conditions | temperature | Concentrate | 80% dilution | Concentrate | 80% dilution |
| No protection | 4° C. | Stable | Stable | Stable | Stable |
| | 25° C. | Stable | Stable | Stable | Stable |
| | 40° C. | Yellowish | N/A | Yellowish | N/A |
| 600 ppm α-tocopherol | 4° C. | Stable | Stable | Stable | Stable |
| | 25° C. | Stable | Stable | Stable | Stable |

TABLE 5-2-continued

Stability of CBD-loaded media

| | Incubation | 5CS | | AX2 | |
|---|---|---|---|---|---|
| Extraction Conditions | temperature | Concentrate | 80% dilution | Concentrate | 80% dilution |
| acetate | 40° C. | Yellowish | Stable | Yellowish | Stable |
| Nitrogen atmosphere | 4° C. | Stable | Stable | Stable | Stable |
| | 25° C. | Stable | Stable | Stable | Stable |
| | 40° C. | Stable | Yellowish | Stable | Yellowish |

As clearly seen, the CBD-loaded media are stable over a wide variety of conditions, namely most of the tested samples remained transparent, without any indication of phase separation or precipitation.

Long-Term Stability

5CS and AX1 extraction media (see Table 1 above) were used to extract CBD from a plant source according to the following procedure: 1:15 w/w ratio of plant:ME, extraction time of 30 minutes under homogenization at 200° C. Two extraction cycles were carried out, and samples were collected for each cycles. The samples were incubated at three different temperature (4, 25 and 40° C.) for 70 days. The samples were not diluted (i.e. the test was carried out on concentrate samples).

Figure 15A:
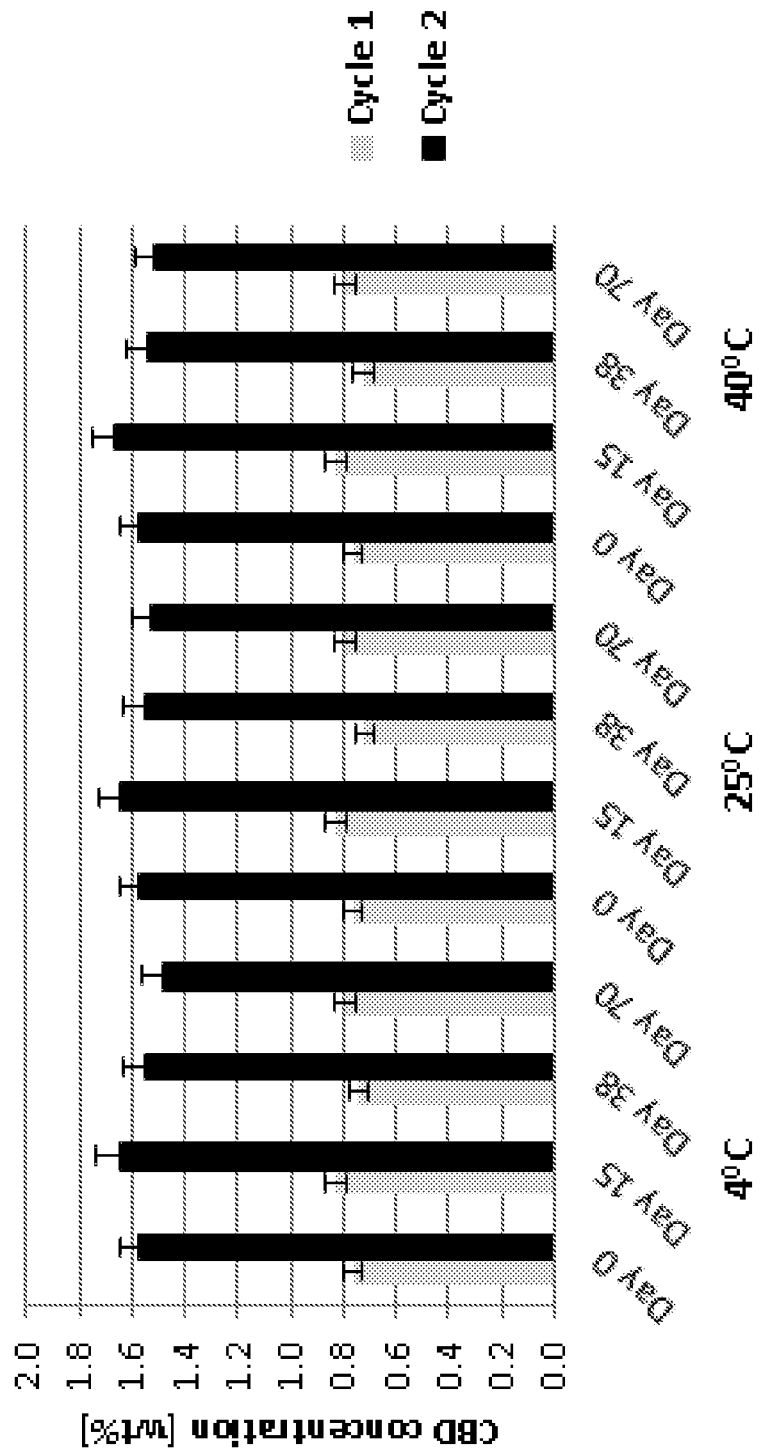
FIGS. 15A-15B show stability test results for 70 days carried out on CBD-loaded AX-1 and 5CS concentrates, respectively.
Figure 15B:
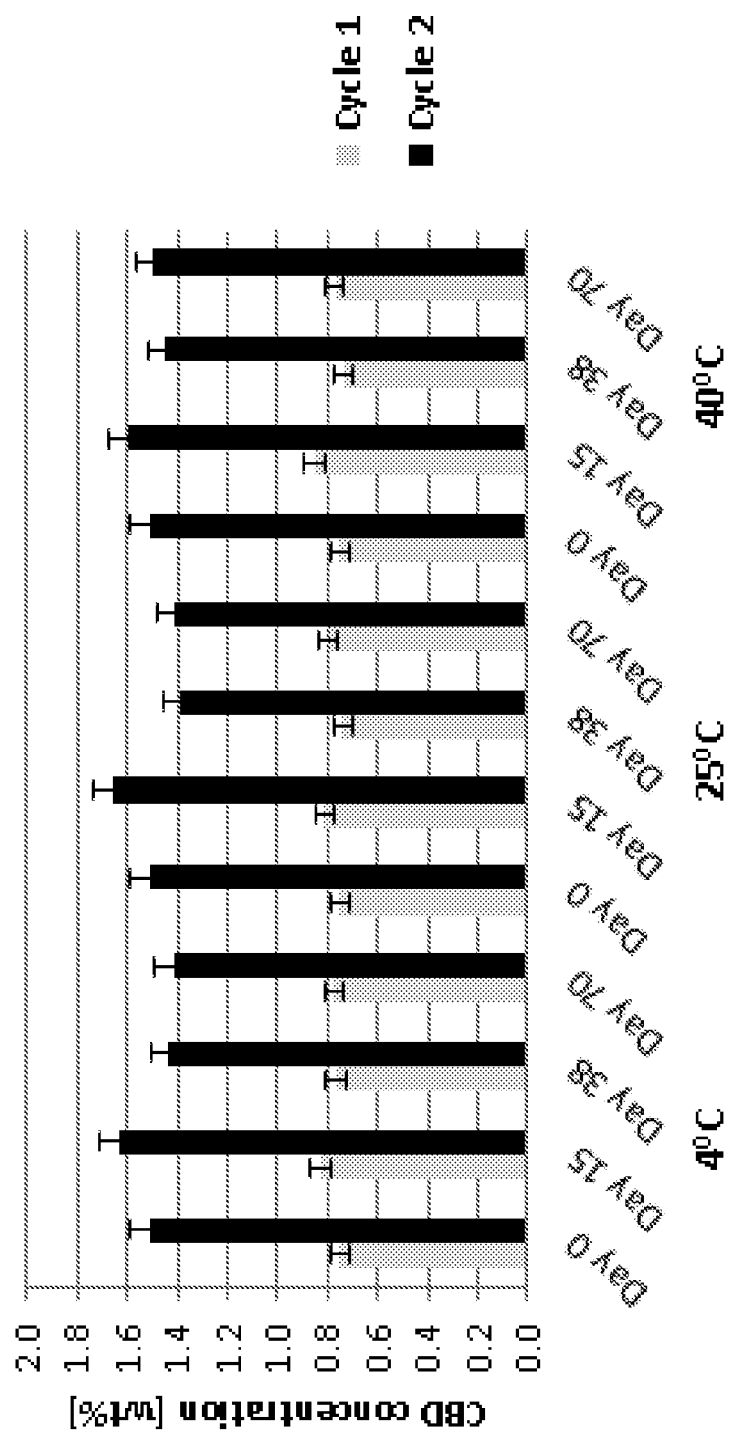

As clearly seen in FIGS. 15A and 15B, the CBD-loaded media in concentrate form are stable over a long period of time, with no change in color or observance of phase separation or precipitation.

PK Study

The pharmacokinetic (PK) profile was assessed by measuring the CBD concentration in plasma after oral administration of AX-1 and 5CS CBD-loaded formulations, as compared to CBD solubilized in olive oil.

Male rats (250 g on average) were used for this PK study, which was carried out in two stages: in the first stage, crystalline CBD solubilized in olive oil was administered orally to the rats, and at a second stage either AX-1 or 5CS CBD-loaded formulations were orally administered via gavage. Blood samples were collected at different time points into heparinized EDTA-K3 tubes and stored on ice. The plasma was separated from each sample by pre-cold centrifugation at 3,000 rpm and stored in clean sterilized tubes at −80±10° C. The rats were sacrificed after 24 from administration.

Figure 16:
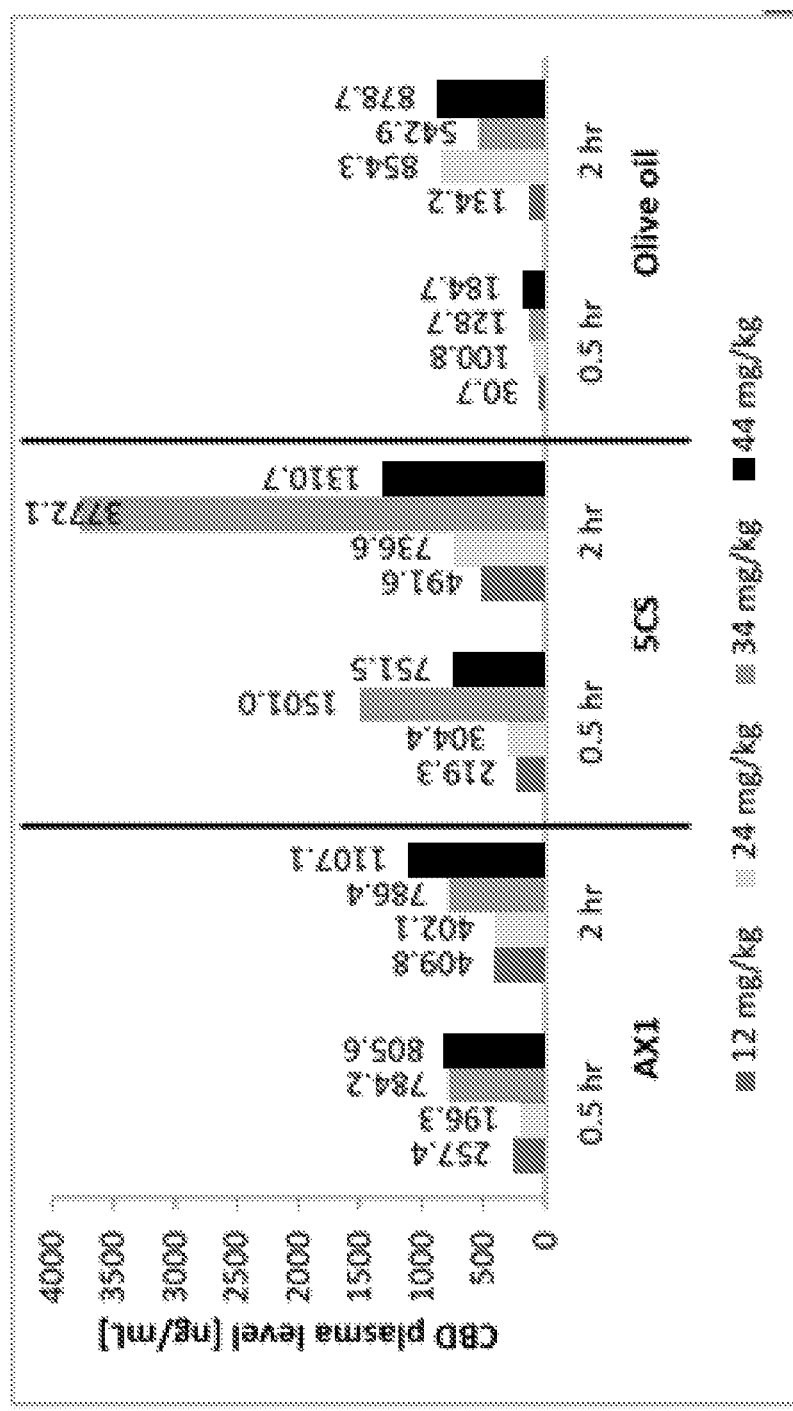
FIG. 16 shows CBD levels in plasma at 0.5 and 2 hours from administration of CBD-loaded AX-1, CBD-loaded 5CS and crystalline CBD solubilized in olive oil (reference) formulations, in samples taken from rats.

FIG. 16 shows the CBD levels in plasma at 0.5 and 2 hours after administration of different doses of the formulations. For both AX-1 and 5CS formulations, the CBD concentration measured in the plasma was higher after 0.5 hr, compared to CBD solubilized in olive oil. After 2 hr from administration, the CBD plasma level was similar for AX-1 and olive oil, while 5CS system showed significant increase in CBD concentration.

Thus, formulations of this disclosure show rapid bioavailability and increase levels of CBD in the plasma compared to olive oil solutions, with Tmax of 0.5 vs. app. 4 hrs.

In-Vivo Studies

Response to Pain

Response to pain and anti-inflammatory activity in mice of the extracted cannabis plant source (CBD-loaded) media of this disclosure were assessed by oral administration of extraction from a cannabis plant using 5CS extraction media compared to traditional ethanol extraction.

5CS extraction medium and ethanol extraction were prepared separately at four different concentrations which were equivalent to 5, 10, 25 and 50 mg plant material/kg body weight rat according to the following protocol.

Three female Sabra mice at the age of 8 weeks old were maintained for 7 days in the SPF unit prior to study initiation. 40 µl of 1.5% (w/v) Zymosan A (sigma) suspended in 0.9% saline was injected into the sub-planter surface of the right hind paw of each mouse. Immediately after induction, extraction from a cannabis plant source was given orally to the inflammation induced mice. Extraction was performed by traditional ethanol extraction or by '5CS Extraction Medium'. As a positive control three induced mice were left untreated. The mice treated with the 'extracted medium' were administered orally directly with loaded 5CS, while the 'ethanol extraction' the ethanol was first evaporated and the precipitated material was re-suspended in olive oil.

The therapeutic effect was evaluated in various administration dosage of extracted material including 10, 25 and 50 mg extracted plant source to each kg body weight. After 6 hr from treatment the swelling of the inflammated paw was measured using a caliper. In addition, after 24 hour form treatment, TNF-α (tumor necrosis factor) levels were measured using an ELISA kit (R&D system) according to the manufacturer's instruction.

Figure 17:
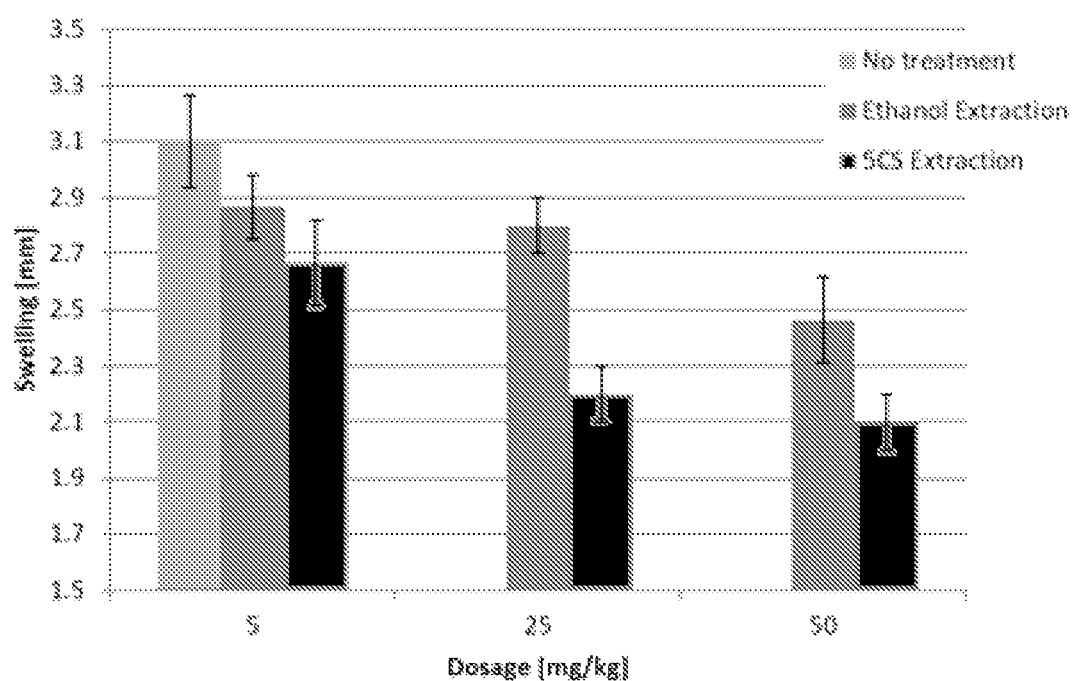
FIG. 17 shows TNF-α plasma levels form mice with induced acute paw inflammation as measured in blood samples taken after 24 hours of oral treatment with '5CS extracted media' or 'ethanol extraction' at a dosage of 5, 25 and 50 mg plant source to kg body weight.
Figure 18:
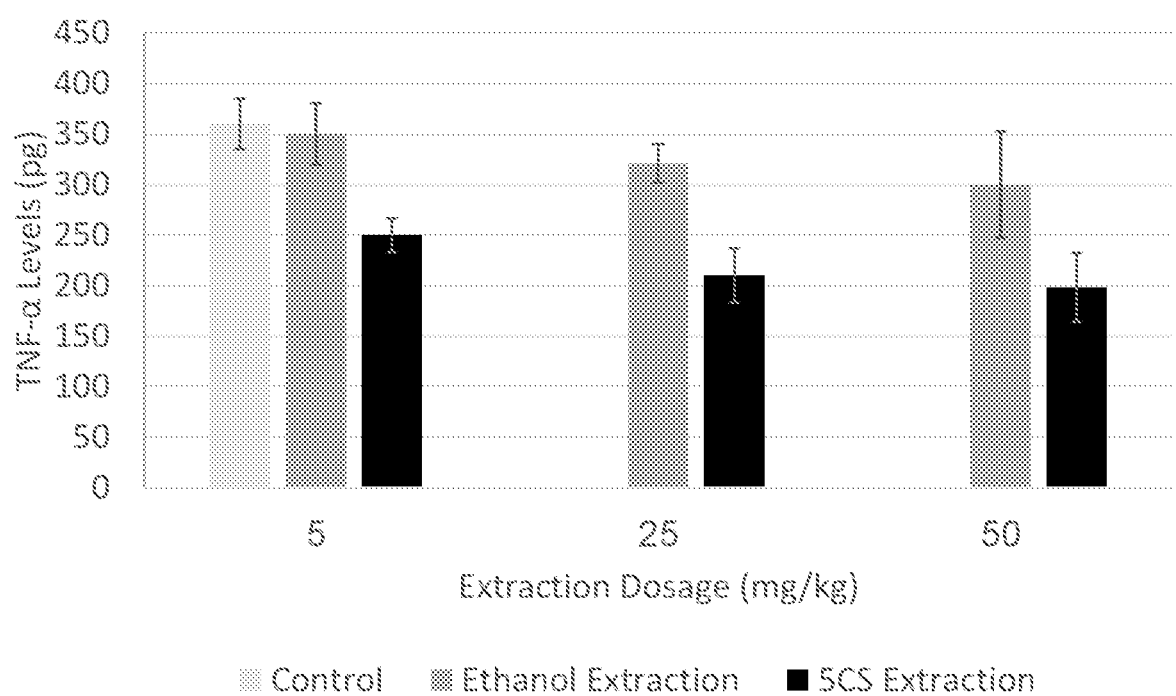
FIG. 18 shows the paw-thickness of inflammated paw in mice treated with '5CS extraction media' medium compared to extraction with ethanol dissolved in olive oil as measured 6 hours after treatment.
Figure 19:
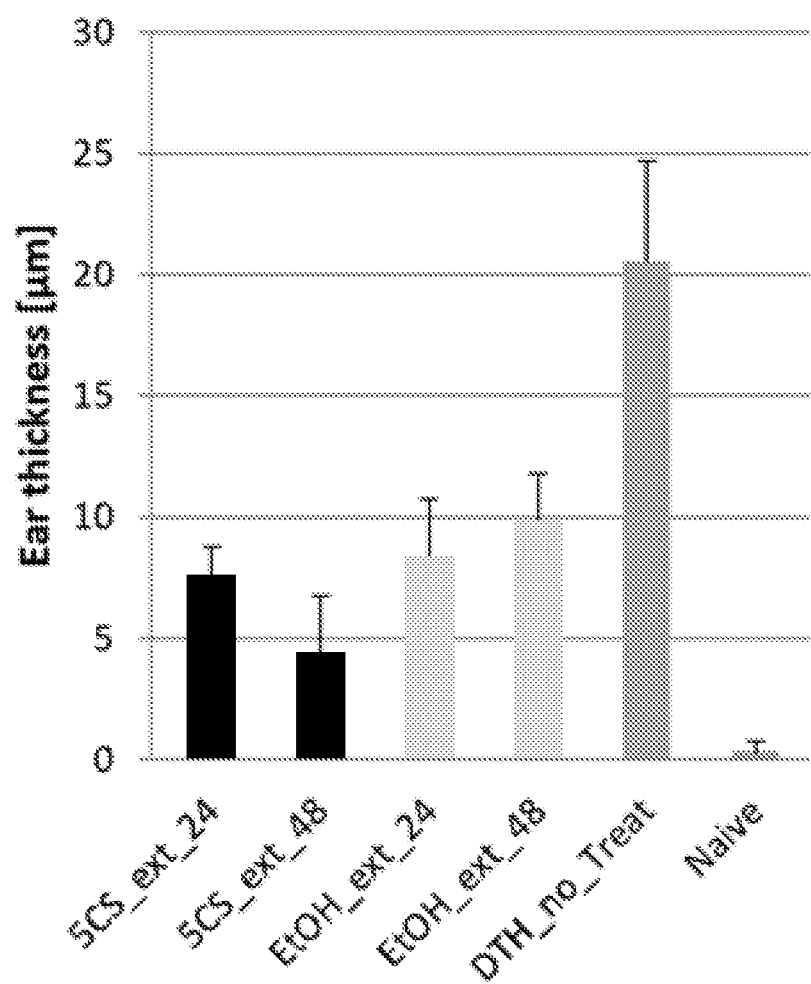
FIG. 19 shows the measured ear thickness of DHT-induced rats.
Figure 20A:
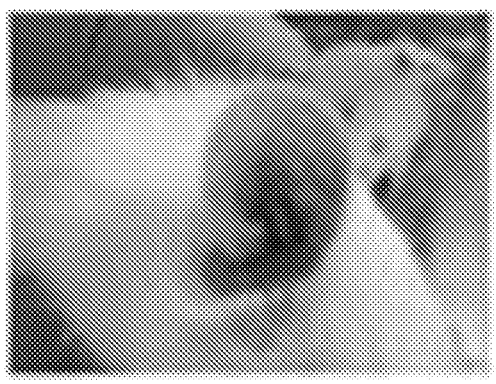
FIGS. 20A-D are pictures of rats' ears in DHT test: 24 mg/kg BW of 5CS formulation (FIG. 20A), 48 mg/kg BW of 5CS formulation (FIG. 20B), non-treated DHT-induced (FIG. 20C), and naïve rats (FIG. 20D).
Figure 20B:
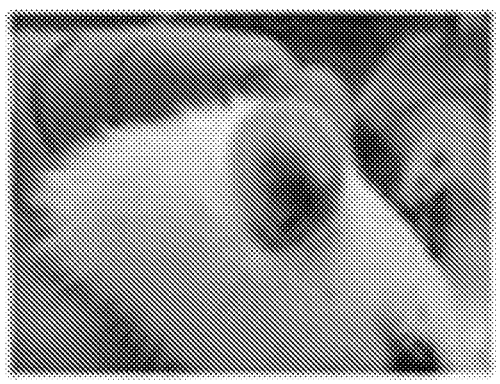
Figure 20C:
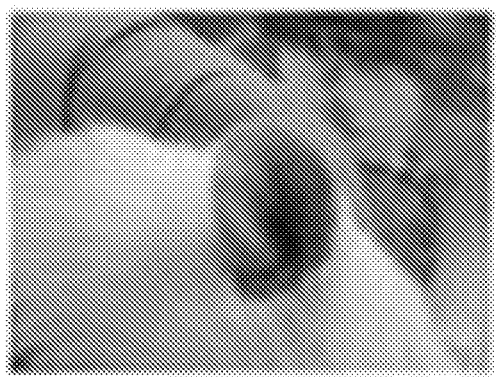
Figure 20D:
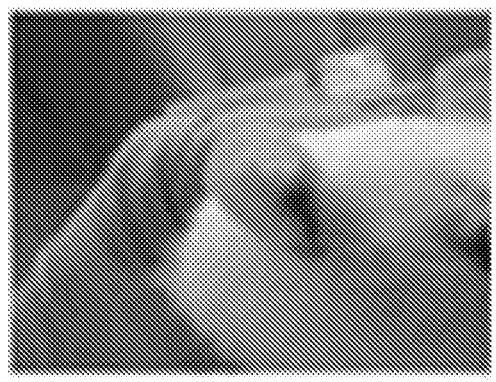

TNF-α was assessed by ELISA kit of plasma samples taken 24 hours after oral treatment. FIG. 17 shows the TNF-α levels for 5CS extracted media compared to extraction by ethanol and dispersion in olive oil. FIG. 18 shows the paw-thickness of inflammated paw in mice treated with extracted medium 5CS compared to extraction by ethanol dispersed in olive oil.

Administrating '5CS extracted medium' significantly reduced the paw's swelling (compared to the control untreated mice) within all given dosage (5, 25 and 50 mg/kg) in comparison to the ethanol extraction treated mice which showed a much lesser reduction. These results indicate that the inflammation is reduced in greater efficiency using the 'extraction medium' compared to extraction with ethanol. TNF-α plasma levels were considerably lower in the mice treated with the '5CS extraction medium' compared to that extracted with ethanol at all dosage tested.

The reduction in TNF-α levels (250 compared to 350 pg of control untreated mice) using 5CS extraction medium was seen even when using relatively low dosage (5 mg/kg), while using ethanol extraction at the same dosage did not affect the TNF-α levels, which were almost similar to those measured in the untreated mice (320 vs 350 pg, respectively).

As seen from FIG. 18, in all dosages tested, mice administered with the CBD-loaded medium of the present disclosure showed lower TNF-α levels after 24 hours from administration resulting in reduced inflammation compared to that of the CBD extracted by ethanol. This attests to the improved extraction, release and permeation (performance) of the extraction media.

Further, as seen in FIG. 17, mice administered with the extraction medium of the present disclosure showed a more significant reduction in paw thickness in all dosages tested as compared to identical dosages of CBD extracted in ethanol and dissolved in olive oil. Namely, the formulations of the present disclosure have an improved anti-inflammatory activity as compared to standard ethanol CBD extractions.

Delayed-Type Hypersensitivity (DTH)

CBD was shown to reduce inflammation response and pain-effected by inflammatory reaction. Without wishing to be bound by theory, inflammation reduction is achieved by various mechanisms, including agonist and antagonist binding to CB1 receptors, adenosine receptors and other GPCRs, involving the reduction of inflammatory cytokines and chemokines levels, such as IL-2, IL-6, TNF-α, MCP-1, etc.

The therapeutic effect of oral administration of CBD-loaded formulations of this disclosure as anti-inflammatory agents. The CBD effect was evaluated using rat model of inflammation—Delayed Type Hypersensitivity (DHT) model. In this test, the reduction in ear swelling after inflammation-induction following treatment was measured.

The belly of male rats (average weight 250 g) was shaved and challenged 10 times with 500 µl of 2% oxazolone (400 mg oxazolone dissolved in 16 ml acetone and 4 ml mineral oil). The next day (referred to herein as day 1), 500 µl of CBD formulation oral treatment was given via gavage. On day 6, the ear thickness of the rats was measured using a caliper.

Rats were challenged with another dose of 50 µl of 0.5% oxazolne, and a second oral treatment of 500 µl CBD formulation was administered 2-hours after challenge. The ear thickness was measured again 12 and 24 hours after challenge, and blood samples were taken for serum preparation.

Samples composition: two doses were administered of extracted CBD in 5CS with a dose of 24 mg/kg BW and 48 mg/Kg BW (BW=Body Weight), compared to control of Naïve rats and rats with DTH-induction that were not given any treatment.

As seen in FIGS. 19 and 20A-D, a significant reduction in ear thickness and inflammatory appearance (redness and edema) as a result of the treatment with CBD extracted with 5CS was obtained compared to DTH-induced rats that were not treated. The anti-inflammatory effect of CBD extracted with 5CS is more significant than that seen for Ethanol extractions with both dose regiments.

The invention claimed is:

1. A process for the extraction of cannabidiol from cannabis to yield a medium in microemulsion form which is devoid of water and enriched in cannabidiol, the process consisting essentially of:
   (a) heating cannabis to a temperature of between about 90° C. and 180° C. for about 5 minutes to 240 minutes, to convert cannabidiolic acid in the cannabis into cannabidiol thereby obtaining cannabis rich in cannabidiol;
   (b) mixing a first quantity of the cannabis rich in cannabidiol and a first quantity of an extraction medium consisting essentially of at least one oil, at least one hydrophilic surfactant and at least one co-surfactant to form a first microemulsion mixture which is devoid of water;
   (c) homogenizing the first microemulsion mixture under conditions to maintain the first microemulsion mixture devoid of water, wherein the homogenization is carried out at a pressure of between about 500 psi and 6,000 psi and at a temperature of between about 5° C. and about 70° C., for a period of time of between about 1 minute and about 60 minutes;
   (d) separating a cannabis biomass slurry from the first microemulsion mixture to obtain a first cannabidiol-loaded medium in a microemulsion form devoid of water;
   (e) mixing the cannabidiol-loaded medium in a microemulsion form that is devoid of water with a second quantity of cannabis to obtain a second mixture;

(f) homogenizing the second mixture; and
(g) separating a cannabis biomass slurry from the second mixture to obtain a medium in a microemulsion form which is devoid of water and enriched in cannabidiol,
wherein the cannabidiol-loaded medium is in a microemulsion form which is devoid of water,
wherein the at least one oil is selected from the group consisting of medium chain triglycerides, olive oil, soybean oil, canola oil, cotton oil, palmolein, sunflower oil, corn oil, isopropyl myristate, oleyl lactate, coco caprylocaprate, hexyl laurate, oleyl amine, oleic acid, oleyl alcohol, linoleic acid, linoleyl alcohol, ethyl oleate, hexane, heptanes, nonane, decane, dodecane, D-limonene, triacetin, neem oil, lavender oil, peppermint oil, anise oil, menthol, capsaicin, grape seed oil, pomegranate oil, avocado oil, sesame oil, fish oil, omega oils and omega fatty acids;
wherein the at least one hydrophilic surfactant is selected from the group consisting of polyoxyethylene sorbitan monolaurate, polyoxyethylene sorbitan monopalmitate, polyoxyethylene sorbitan monooleate, polyoxyethylene esters of saturated and unsaturated castor oil, ethoxylated monoglycerol esters, glycerol, ethoxylated fatty acids, ethoxylated fatty acids of short, medium and long chain fatty acids; and
wherein the at least one co-surfactant is at least one polyol.

2. The process of claim 1, wherein the cannabidiol-loaded medium has a tetrahydrocannabinol content of at most 3 wt %.

3. The process of claim 1, wherein the cannabinoid-loaded medium has a cannabidiol content between about 0.1 and 12 wt %.

4. The process of claim 1, wherein the separating step comprises centrifuging the mixture.

5. The process of claim 4, wherein the centrifuging the mixture is followed by filtering.

6. The process of claim 1, wherein the weight ratio (wt./wt.) of cannabis to said first quantity of extraction medium is between 1:5 and 1:100.

7. The process of claim 1, wherein the step sequence (e)-(g) is repeated between 3 and 7 times.

* * * * *